(12) United States Patent
Paul, Jr. et al.

(10) Patent No.: US 8,128,686 B2
(45) Date of Patent: Mar. 6, 2012

(54) BRANCHED VESSEL PROSTHESIS

(75) Inventors: Ram H. Paul, Jr., Bloomington, IN (US); Sean D. Chambers, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/425,911

(22) Filed: Apr. 17, 2009

(65) Prior Publication Data
US 2009/0264991 A1  Oct. 22, 2009

Related U.S. Application Data

(60) Provisional application No. 61/046,211, filed on Apr. 18, 2008.

(51) Int. Cl.
*A61F 2/06* (2006.01)
(52) U.S. Cl. ............... 623/1.35; 623/1.16; 623/1.24
(58) Field of Classification Search ............ 623/241.35, 623/1.11, 1.15–1.18, 1.24, 1.35
See application file for complete search history.

(56) References Cited

U.S. PATENT DOCUMENTS

| | | | |
|---|---|---|---|
| 4,580,568 A | 4/1986 | Gianturco | 128/345 |
| 4,675,361 A | 6/1987 | Ward, Jr. | 525/92 |
| 4,800,603 A | 1/1989 | Jaffe | 8/94.11 |
| 4,902,508 A | 2/1990 | Badylak et al. | 424/95 |
| 5,411,552 A | 5/1995 | Andersen et al. | 623/2 |
| 5,554,389 A | 9/1996 | Badylak et al. | 424/558 |
| 5,595,571 A | 1/1997 | Jaffe et al. | 8/94.11 |
| 5,597,378 A | 1/1997 | Jervis | 606/78 |
| 5,720,777 A | 2/1998 | Jaffe et al. | 623/2 |
| 5,843,180 A | 12/1998 | Jaffe et al. | 623/2 |
| 5,843,181 A | 12/1998 | Jaffe et al. | 623/2 |
| 5,855,601 A | 1/1999 | Bessler et al. | 623/2 |
| 5,993,844 A | 11/1999 | Abraham et al. | 424/423 |
| 6,056,775 A * | 5/2000 | Borghi et al. | 623/1.16 |
| 6,099,567 A | 8/2000 | Badylak et al. | 623/13 |
| 6,206,931 B1 | 3/2001 | Cook et al. | 623/23.75 |
| 6,231,598 B1 | 5/2001 | Berry et al. | 623/1.15 |
| 6,299,635 B1 | 10/2001 | Frantzen | 623/1.17 |
| 6,409,752 B1 | 6/2002 | Boatman et al. | 623/1.15 |
| 6,440,164 B1 | 8/2002 | DiMatteo et al. | 623/1.24 |

(Continued)

FOREIGN PATENT DOCUMENTS

FR   2 722 678 A1   1/1996

(Continued)

OTHER PUBLICATIONS

Dougal et al., "Stent Design: Implications for Restenosis," Rev. Cardiovasc Med. 3 (suppl. 5), S16-S22 (2002).

(Continued)

*Primary Examiner* — David Isabella
*Assistant Examiner* — Yashita Sharma
(74) *Attorney, Agent, or Firm* — Buchanan Nipper

(57) ABSTRACT

The present disclosure describes an implantable branched vessel prosthesis, such as a prosthetic valve, having both a radially expandable annular portion and a laterally extendable branch portion. Methods of delivering the branched vessel prosthesis to a branched body vessel are also provided, as well as delivery systems comprising the branched vessel prosthesis. The branched vessel prostheses are useful, for example, as implantable prosthetic venous valves for treating venous valve insufficiency. The delivery system is configured to deploy independently both the annular portion within a primary vessel and the branch portion within a branch vessel with only one delivery system.

16 Claims, 12 Drawing Sheets

U.S. PATENT DOCUMENTS

| | | | |
|---|---|---|---|
| 6,464,720 B2 | 10/2002 | Boatman et al. | 623/1.15 |
| 6,508,833 B2 | 1/2003 | Pavcnik et al. | 623/1.15 |
| 7,087,089 B2 | 8/2006 | Patel et al. | 623/23.72 |
| 7,232,462 B2 * | 6/2007 | Schaeffer | 623/11.11 |
| 7,744,643 B2 * | 6/2010 | Hegg | 623/1.35 |
| 2001/0039450 A1 | 11/2001 | Pavcnik et al. | 623/1.24 |
| 2002/0065552 A1 | 5/2002 | Jayaraman et al. | 623/1.46 |
| 2003/0120263 A1 | 6/2003 | Ouriel et al. | 606/1 |
| 2004/0138737 A1 * | 7/2004 | Davidson et al. | 623/1.35 |
| 2004/0180042 A1 | 9/2004 | Cook et al. | 424/93.7 |
| 2004/0260389 A1 | 12/2004 | Case et al. | 623/1.24 |
| 2006/0095118 A1 | 5/2006 | Hartley | 623/1.35 |
| 2007/0021826 A1 | 1/2007 | Case et al. | 623/1.15 |
| 2007/0038291 A1 | 2/2007 | Case et al. | 623/1.16 |
| 2007/0043425 A1 | 2/2007 | Hartley et al. | 623/1.12 |
| 2007/0100435 A1 | 5/2007 | Case et al. | 623/1.24 |
| 2007/0162103 A1 | 7/2007 | Case et al. | 623/1.13 |
| 2007/0219621 A1 | 9/2007 | Hartley et al. | 623/1.13 |
| 2007/0225798 A1 | 9/2007 | Gregorich | 623/1.35 |
| 2007/0288082 A1 | 12/2007 | Williams | 623/1.11 |
| 2008/0294234 A1 | 11/2008 | Hartley et al. | 623/1.12 |
| 2009/0105810 A1 | 4/2009 | Jaffe | 623/1.24 |
| 2009/0105813 A1 | 4/2009 | Chambers et al. | 623/2.12 |

FOREIGN PATENT DOCUMENTS

| | | |
|---|---|---|
| WO | WO 95/31945 A1 | 2/1996 |
| WO | WO 00/47134 A1 | 8/2000 |
| WO | WO 03/002165 A1 | 1/2003 |
| WO | WO 2007/108857 A1 | 9/2007 |

OTHER PUBLICATIONS

BS EN ISO 11135-1:2007 "Sterilization of health care products-Ethylene oxide-Part 1: Requirements for development, validation and routine control of a sterilization process for medical devices."

* cited by examiner

BRANCHED VESSEL PROSTHESIS

CROSS-REFERENCE TO RELATED APPLICATIONS

This application claims priority and the benefit of provisional U.S. patent application Ser. No. 61/046,211, filed Apr. 18, 2008, which is incorporated herein by reference in its entirety.

FIELD OF THE INVENTION

The present disclosure pertains to implantable prosthetic devices for placement at a branched vessel site as well as related methods of treatment. Delivery systems for placement of branched vessel prostheses are also provided.

BACKGROUND

Intraluminally implantable frames may be implanted to treat a variety of conditions in a variety of fields. Frames implanted in vessels, ducts or channels of the human body can form part of a valve to regulate fluid flow within a body lumen or as scaffolding to maintain the patency of the vessel, duct or channel lumen. Implantable frames can also support a valve or valve leaflets for regulating fluid flow within a body lumen or for dilating a body lumen. One or more flexible valve leaflets can be attached to an implantable frame to form a medical device useful as an artificial valve. A variety of other implantable prostheses, such as stents, grafts and the like, also comprise an implantable frame placed within the body to improve the function of a body lumen.

The venous system includes a series of valves that function to assist the flow of blood returning to the heart. These natural valves are particularly important in the lower extremities to prevent blood from pooling in the lower legs and feet during situations, such as standing or sitting, when the weight of the column of blood in the vein can act to prevent positive blood flow toward the heart. However, with gradual dilation of the veins, thrombotic events, or other conditions which prevent the leaflets of the native valves from closing properly, individuals can develop a venous valve-related conditions.

In the condition of venous valve insufficiency, the valve leaflets do not function properly. Incompetent venous valves can result in symptoms such as swelling and varicose veins, causing great discomfort and pain to the patient. If left untreated, venous valve insufficiency can result in leakage to excessive retrograde venous blood flow through incompetent venous valves, which can cause venous stasis ulcers of the skin and subcutaneous tissue. Venous valve insufficiency can occur, for example, in the superficial venous system, such as the saphenous veins in the leg, or in the deep venous system, such as the femoral and popliteal veins extending along the back of the knee to the groin. Elevation of the feet and compression stocking can relieve symptoms, but do not treat the underlying disease. Untreated, the disease can impact the ability of individuals to perform in the workplace or maintain their normal lifestyle.

Examples of venous valve-related conditions are chronic venous insufficiency and varicose veins. Chronic venous insufficiency is divided into two forms, secondary and primary, depending on the cause of the disease. In secondary disease, destruction of the valves is caused by the incidence of deep and/or superficial vein thrombosis. For instance, chronic thrombosis of the deep vein system can result in the enlargement and/or formation of secondary or collateral veins which bypass the thrombosed primary vein lumen of the deep vein system to allow the return of blood flow to the heart. These secondary veins often are also incompetent and do not impede retrograde flow of blood away from the heart. In some patients with secondary chronic venous insufficiency, the enlargement and/or formation of these secondary veins can result in secondary veins having a diameter approximately equal to the diameter of the primary femoral vein. In this scenario, a dual femoral vein with a well formed bifurcation and confluence is present.

One promising approach to treating venous valve insufficiency includes the implantation of self-expanding or radially-expandable artificial valves that can be placed using minimally invasive techniques. Recently, the development of artificial and biological valves has been employed to provide additional regulation of blood flow within blood vessels, such as veins. There are a variety of these valves described in the art, which are generally designed to allow normal flow of blood back to the heart, while preventing retrograde flow. However, dynamic fluctuations in the shape of the vein pose challenges to the design of implantable devices that conform to the interior shape of the vein. The shape of a lumen of a vein can undergo dramatic dynamic change as a result of varying blood flow velocities, pressures, and volumes therethrough. Implantable intraluminal prosthetic valves should be compliant enough to conform to the changing shape of the vein lumen and prevent irritation of the wall of the vein contacting the valve, but rigid enough to maintain vein patency and/or valve function within the vein. Blood flow within a vein is intermittent and bidirectional, subject to constant fluctuation in pressure and volume. These conditions may present challenges to designing an implantable frame suitable for placement inside the vein. An implantable frame lacking sufficient radial strength may collapse and/or fracture under the repeated fluctuations of vein diameter, while an implantable frame with undesirably high levels of radial strength may lack flexibility and may damage the vein by failing to compress in response to normal fluctuations in the vein diameter. Likewise, an implantable frame with a high surface area contacting the interior wall of a vein may induce inflammation or trauma in the vein wall, while an implantable frame with an insufficient surface area may lack sufficient durability.

What is needed is an intraluminally-placed medical device, such as a support frame, that provides structure for an artificial valve and is configured to distribute stress and strain forces within the frame during dynamic movement of a body vessel and intermittent fluid flow within the body vessel. In addition, medical devices are needed that provide sufficient radial strength to maintain vessel patency at a primary vessel and a secondary vessel, such as in the vicinity of a bifurcation and/or confluence of a vein, while supporting a means for regulating fluid within the primary and/or secondary vessels and/or minimizing irritation to the body vessel after implantation. Further, deployment of such medical devices with one deployment system is needed in order to decrease the time of intervention.

SUMMARY

Accordingly, a branched vessel prosthesis, a delivery system, and methods of use are provided. The branched vessel prosthesis is configured to be implanted at a branch vessel site having a first or primary body vessel and a second or secondary body vessel. For example, if treatment is in the vicinity of a bifurcation and/or confluence of a vein, due to natural vein anatomy, the incidence of chronic deep vein thrombosis, or other causes, the branched vessel prosthesis can provide sufficient radial strength to maintain vessel patency at the first body vessel and the second body vessel while supporting a means for regulating fluid flow with in the primary and/or secondary vessels. The branched vessel prosthesis includes a primary hoop member configured to be implanted into the first body vessel and a branch hoop member coupled to the primary hoop member and configured to be independently implanted in the second body vessel. Preferably, the branch hoop member is self-expandable in order for the branch hoop member to "pop" or "unfold" into the second vessel after orientation and alignment.

In a first embodiment, an intraluminally implantable branched vessel prosthesis is provided with a support frame having an expanded configuration including a branch hoop member extendable from a tubular lumen defined by a pair of primary hoop members. The branched vessel prosthesis may be moveable from a tubular radially compressed configuration, for example within a delivery catheter, to a branch radially expanded configuration within a body vessel. In the radially compressed configuration, the branch hoop member may be positioned between the pair of primary hoop members. The primary hoop members may be a ring frame structure adapted to radially expand independently during radial expansion of the branched vessel prosthesis. The primary hoop members are preferably longitudinally spaced a distance from each other that is greater than the diameter of the branch hoop member in the second position such that the branch hoop member is positionable between the primary hoop members. The branch hoop member may be a separate frame structure connected to the primary hoop members and moveable between a first position between the primary hoop members in a compressed configuration and a second position extending away from at least one of the primary hoop members. The branch hoop member may extend at a branching angle suitable to form a bifurcated tubular prosthetic structure. The branch hoop member and the primary hoop members are attached via at least one flexible member. The flexible member can be a wire strut, suture, graft material, or the like. The wire strut can have a bend or curvature or be bendable to conform around the branching angle. Preferably, the branched vessel prosthesis has a frame adapted to permit the lateral extension of the branch hoop member independent of the radial compression of one or both primary hoop members. The branch hoop member may have a length that is less than the primary hoop members in the radially compressed configuration such that the branch hoop member is positionable within the primary lumen when the primary hoop members are in the radially compressed configuration. The length can be about 25-75% the diameter of the primary hoop members in the radially compressed configuration. Optionally, the support frame may also include more than two primary hoop members and/or multiple branch hoop members.

In addition to the support frame, the branched vessel prosthesis may include one or more valves to regulate fluid flow through a primary lumen defined by the primary hoop members in the bifurcated radially expanded configuration. A valve may also be located in the branch hoop member in order to regulate fluid flow in the branch lumen. The valves preferably include one or more valve leaflets having a base attached to the support frame and a free end extending in the lumen and movable between an open and closed configuration.

In a second embodiment, an intraluminal prosthesis delivery system is provided. The system may be configured to retain the branched vessel prosthesis in the radially compressed configuration with the branch hoop member positioned between the pair of radially compressed primary hoop members. Preferably, the system is adapted to permit expansion of individual primary hoop members and lateral extension of the annular branch member independent of each other. For example, the delivery system may include a delivery catheter with a distal portion adapted to receive and retain the intraluminal prosthesis in the radially compressed configuration. The delivery catheter preferable includes a retractable outer sheath disposed about an inner shaft portion defining a wire guide lumen. The outer sheath and/or the inner shaft portion can have an elliptical cross section around the branched vessel prosthesis in the radially compressed configuration. In the radially compressed configuration, the branch hoop member does not fit around the inner shaft portion, but is positioned to one side of the inner shaft portion where the branch hoop member is retained between the primary hoop members, the inner shaft portion and the outer sheath.

In addition, the delivery catheter may also include a means for retaining the branch hoop member in the first position, between the pair of primary hoop members, such as a hook or other structure adapted to mechanically restrain lateral movement of the branch hoop member from the first position. In one example, the means for retaining includes a tethering device having a wire member extending along the delivery catheter and a grasping member coupled to the wire member and removably attached to the branch hoop member. The grasping member can be coupled to the distal and/or proximal portion of the branch hoop member. Optionally, a trigger wire with or without a loop may be removably attached to the proximal and/or distal portion of the branch hoop member. A retaining ring and/or a loop may also be provided to compress a portion of the branch hoop member.

The delivery system is configured to deploy both primary hoop members of the support frame of the branch vessel prosthesis within the first body vessel and the branch hoop member of the support frame within the second body vessel intersecting the first body vessel at one time. This avoids the need to have multiple delivery systems: one for the deployment of the primary hoop members of the support frame, and one for the deployment of the branch hoop member. Time for the procedure is also saved as the branch hoop member is coupled to the primary hoop members before the procedure and not during the procedure. The branch hoop member is sized and configured to be compressed within a space defined not only by the primary hoop members that are also in a compressed configuration, but also by the inner shaft and the outer sheath of the delivery system. The branch hoop member is coupled to at least one of the primary hoop members by a flexible member. Preferably, the flexible member is a self-expanding strut configured to permit the bending of the strut when the primary hoop member is compressed and to permit self-expansion such that the branch hoop member can "pop" or "unfold" into the second vessel after alignment. The delivery system is also configured to allow independent expansion of the primary hoop members and the branch hoop member. This can give greater flexibility for positioning and orienting the branched vessel prosthesis.

In a third embodiment, methods of delivering a branched vessel prosthesis to a branched vessel site are also provided. These methods may include inserting the branched vessel prosthesis into a body, translating the branched vessel prosthesis to a point of treatment at a branched body vessel site, and deploying the branched vessel prosthesis at the point of treatment by expanding the branched vessel prosthesis. The step of deploying the branched vessel prosthesis may include independently performing the following steps: radially expanding at least one primary hoop member(s) and laterally extending a branch hoop member.

DETAILED DESCRIPTION

The following provides a detailed description of embodiments that illustrate preferred variations of the invention. The embodiments described and illustrated herein are exemplary in nature, and are not intended to limit the scope of the invention in any manner. Rather, the embodiments serve simply as examples to aid in enabling one of ordinary skill in the art to make and use the invention.

Figure 1A:
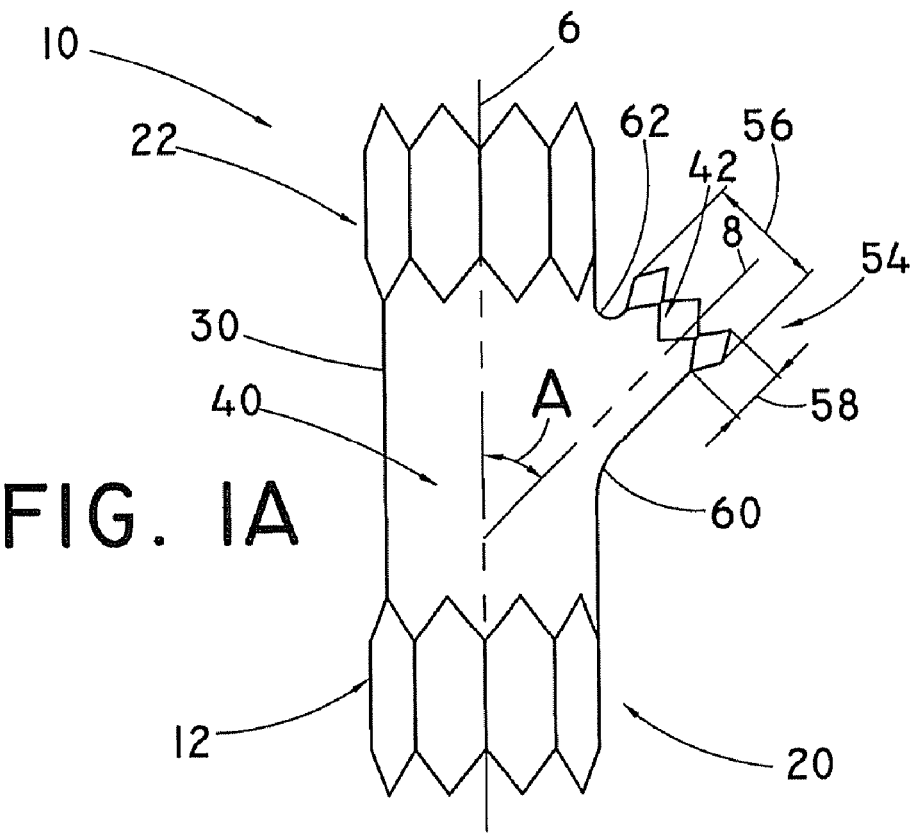
FIG. 1A is a side view of a support frame of a branched vessel prosthesis in a branch radially expanded configuration.
Figure 1B:
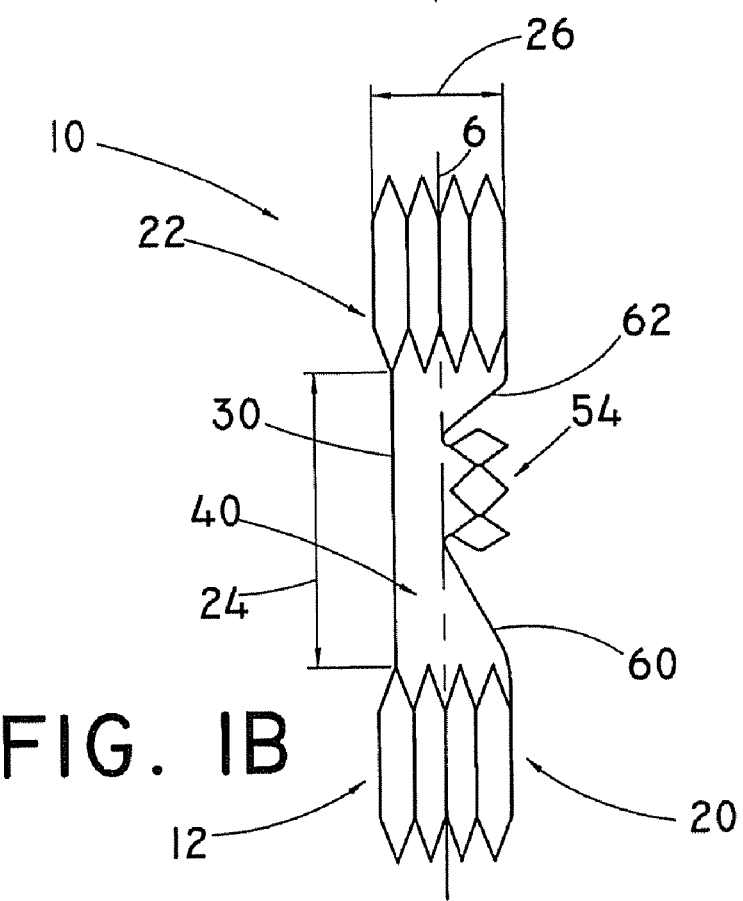
FIG. 1B is a side view of the support frame shown in FIG. 1A in the radially compressed configuration.

FIG. 1A is a side view of a support frame 12 of a branched vessel prosthesis 10 in a bifurcated radially expanded configuration. The support frame 12 includes a first primary hoop member 20 joined to a second primary hoop member 22 by a longitudinal connecting strut 30. The term "primary hoop member" is used throughout the specification to refer to a generally circular (or elliptical) or cylindrical frame structure which resists compression by providing a desired level of radial rigidity after deployment. The primary hoop members 20, 22 are each in a radially expanded configuration and are longitudinally spaced from each other to define a primary lumen 40 around the longitudinal axis 6. The support frame 12 also includes a branch hoop member 54 connected to at least one primary hoop member by at least one flexible strut. FIGS. 1A and 1B illustrate this connection between the branch hoop member 54 and the first primary hoop member 20 by a first flexible connecting strut 60 and the second primary hoop member 22 by a second flexible connecting strut 62. The branch hoop member 54 is shown as a circumferentially enclosed structure defining a branch lumen 42 in communication with the primary lumen 40.

The support frame 12 is moveable between the bifurcated radially expanded configuration and a radially compressed configuration shown in FIG. 1B. Movement from the radially expanded configuration to the radially compressed configuration may be performed in one or more independent steps, including: (1) lateral translation of the branch hoop member 54 radially inward toward the longitudinal axis 6, (2) radial compression of the first primary hoop member 20 toward the longitudinal axis 6 and (3) radial compression of the second primary hoop member 20 toward the longitudinal axis 6. These steps may be performed independent of each other or simultaneously, and may be performed while expanding or compressing the radial profile of the support frame 12. The support frame 12 can be deployed in stages within a body vessel, permitting adjustment of the relative longitudinal spacing of the primary hoop members 20, 22 relative to one another during the deployment process. For example, the first primary hoop member Referring to FIG. 1B, in the radially compressed configuration the primary hoop members 20, 22 remain connected by the longitudinal connecting strut 30 and are disposed around the longitudinal axis 6. Further, the branch hoop member 54 is positioned within the primary lumen 40 between the compressed primary hoop members 20, 22 to define a first position. The primary hoop members 20, 22 can be spaced a longitudinal distance 24 that can be greater than a diameter 56 of the branch hoop member 54 in the second position or the first position such that the branch hoop member is positionable between the primary hoop members. The branch hoop member 54 can have a length 58 that is less than the diameter 26 of the primary hoop members 20, 22 in the radially compressed configuration such that the branch hoop member is positionable within the primary lumen when the primary hoop members is in the radially compressed configuration. The branch hoop member 54 remains connected to the first primary hoop member 20 by the first flexible connecting strut 60, and to the second primary hoop member 22 by the second connecting strut 62. The flexible connecting struts 60, 62 can be bowed inward to accommodate the positioning of the branch hoop member 54 at the first position.

The branch hoop member 54 is moveable between the first position shown in FIG. 1B and a second position shown in FIG. 1A, where the branch hoop member 54 is to be implanted outside the primary lumen 40. In the first position, the branch lumen 42 defined within the branch hoop member 54 about a branch axis 8 which transverses the longitudinal axis 6 of the primary lumen 40. In the second position, the branch lumen 42 can cross the primary lumen 40 at an angle A, as shown in FIG. 1A. The angle A is determined by the angle between a primary body vessel and a secondary body vessel, or alternatively, the angle between the longitudinal axis and branch axis. The movement of the branch hoop member is preferably independent of the radial expansion of the primary hoop members 20, 22. The branch hoop member is shown to have a smaller cross-sectional area or diameter than the primary hoop members. It is appreciated that the branch hoop member size can be substantially identical to the size of the primary hoop members. The length 58 of the branch hoop member is the distance between the distal and proximal ends of the frame structure of the branch hoop member. Preferably, the length 58 is about 25-75%, and most preferably about 30-50%, the diameter 26 of the primary hoop members in the radially compressed configuration. This ensures that there is enough structure to maintain the patency of the branch vessel, while minimizing the amount of space taken by the branch hoop member when in the second position. In addition, the a potion or all of the branch hoop member 32 can be radially compressed in order to better fit within the branch lumen during deployment.

Preferably, the first and second flexible connecting struts 60, 62 are formed from a resilient material. The resilient material provides a bias, such that the branch hoop member 54 assumes the second position in the absence of a means for retaining and/or restraining the branch hoop member in the first position, as described below. For example, the flexible connecting struts 60, 62 may be formed by a superelastic shape memory metal that is heat set in order to conform to the shape of flexible connecting struts 60, 62 shown in FIG. 1A absent a means for retaining and/or restraining these structures in the configuration shown in FIG. 1B. Accordingly, the branch hoop member 54 may be deployed from the first position to the second position by self expansion of the flexible connecting struts 60, 62.

Figure 2A:
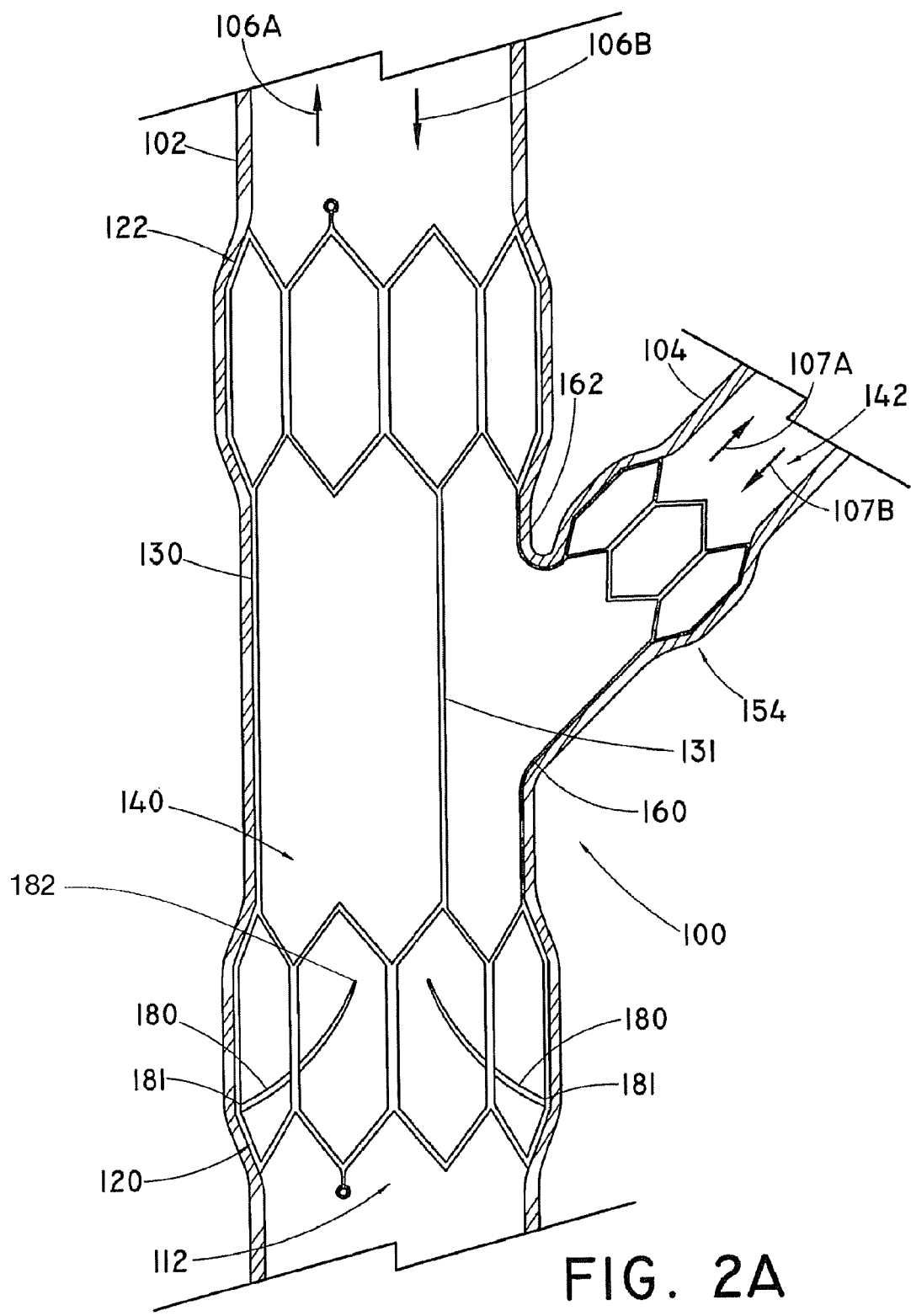
FIG. 2A shows a branched vessel valve prosthesis within a branched body vessel.
Figure 2B:
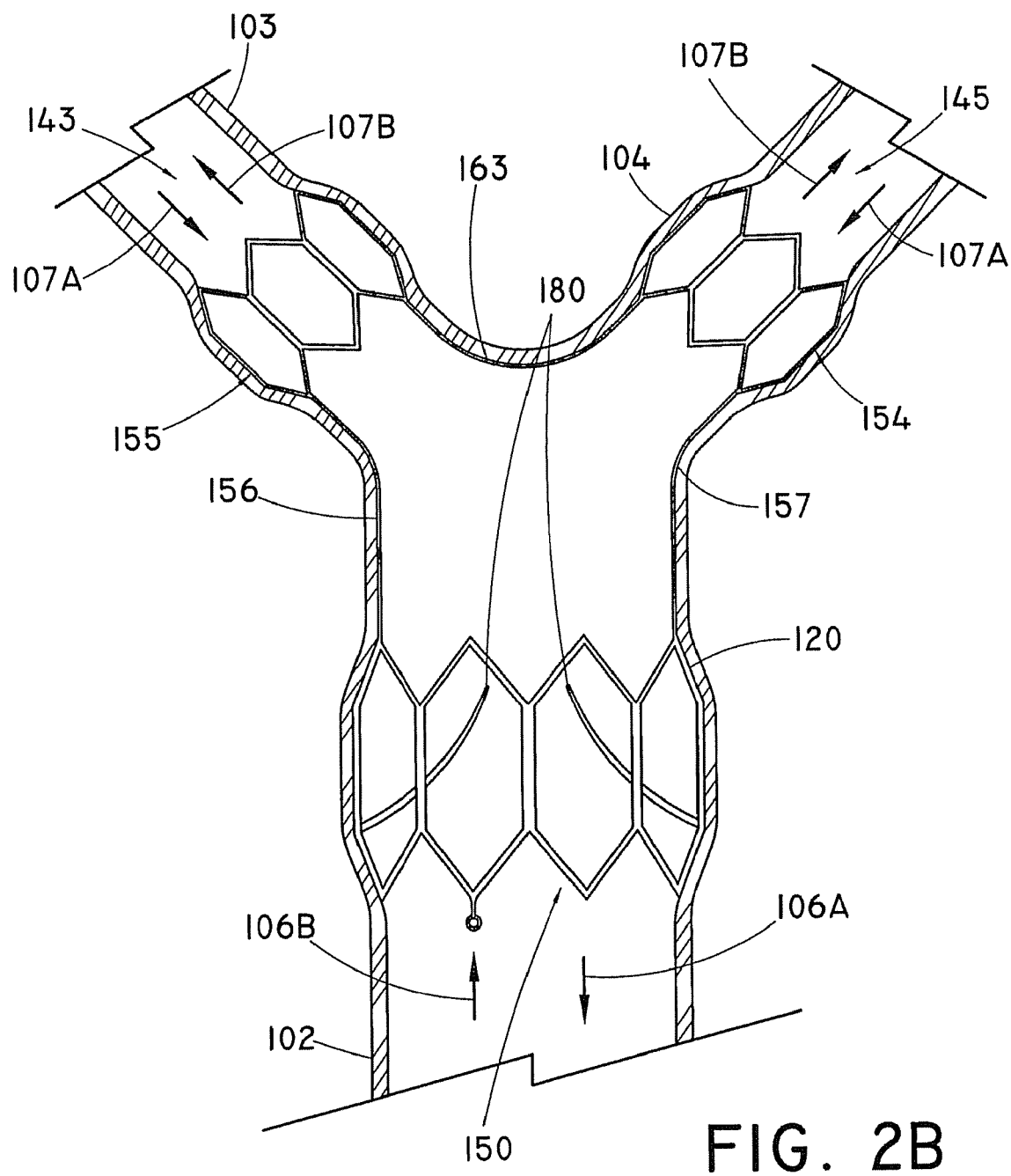
FIG. 2B shows a branched vessel valve prosthesis within another type of branched body vessel.
Figure 2C:
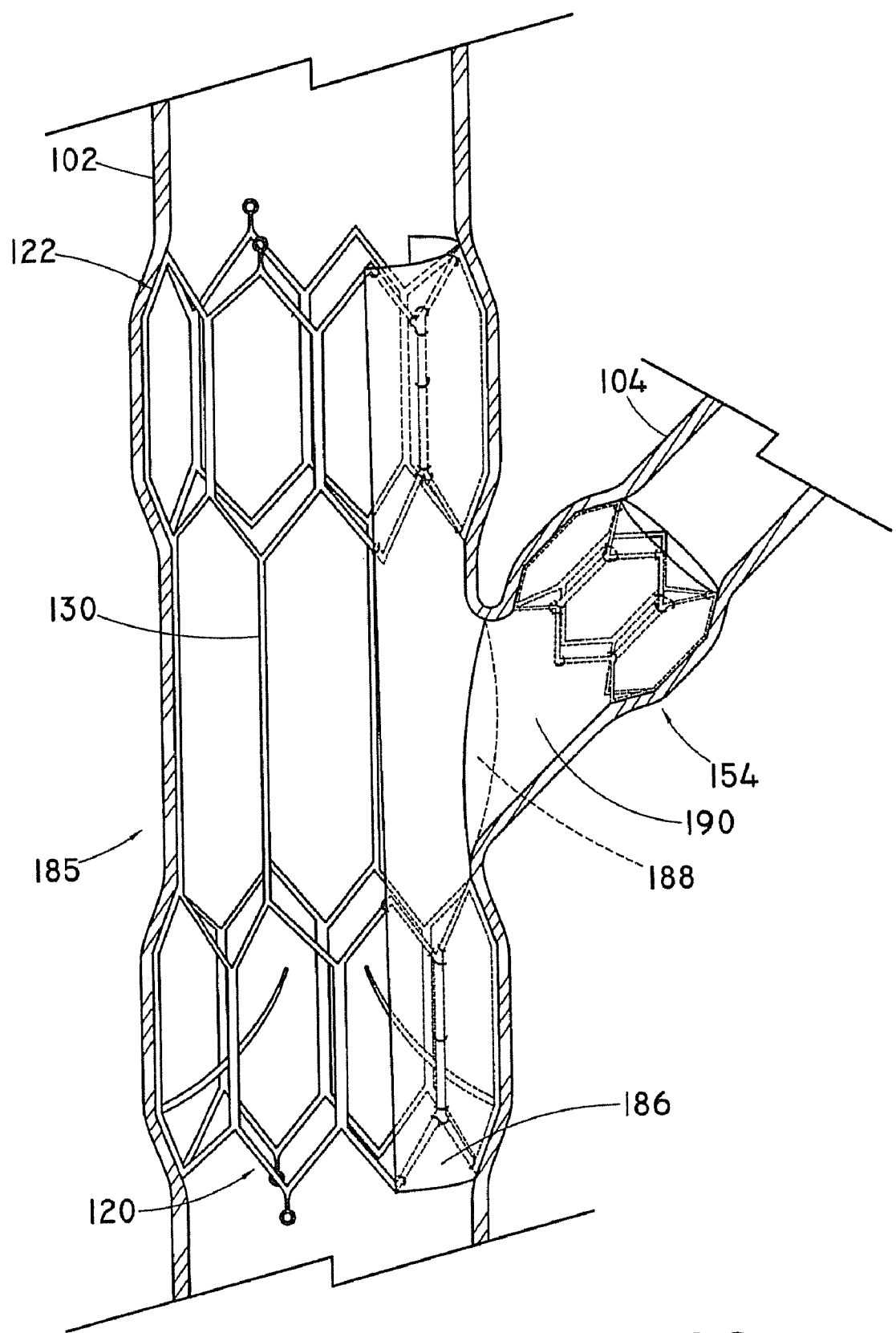
FIG. 2C shows a branched vessel valve prosthesis having graft material within a branched body vessel.

In other embodiments, the flexible connecting struts 60, 62 may include alternative structures, such as tubular graft material, as shown in FIG. 2C, and/or sutures. In these instances, the connecting struts are flexible to allow the branch hoop member to be positioned between the primary hoop members. The branch hoop member can then be implanted within the branch vessel.

The flexible connecting struts 60, 62 can be arcuate, especially in the expanded configuration, in order to conform to the shapes of the primary and branch vessels. FIG. 1A illustrates the flexible connecting strut 62 having a small radius of curvature sufficient to bend around the angle created by the branch vessel and place the branch hoop member 54 within the branch vessel. Optionally, the flexible connecting strut 62 may have one or more bends in order to define the position of the branch hoop member 54 within the branch vessel. The flexible connecting strut 60 is illustrated having a larger radius of curvature than the connecting strut 62, have one bend or multiple bends, to define the position of the branch hoop member 54. The length of the flexible connecting strut 60 is preferably longer than the length of the connecting strut 62, although the length of the struts will depend on the geometry of the primary and branch vessels. Once the length, curvature, and angle of the flexible connecting struts are determined, preferably the flexible connecting struts, made of nitinol, are heat set to conform to the shape after insertion within the body.

The primary hoop members 20, 22 and the branch hoop member 54 each may have an annular configuration selected or optimized for a particular application. Preferably, the structure of these hoop members is selected to provide a radially compressible annular structure that provides a desired degree of hoop strength. The structure should be selected to provide a minimum desired amount of mechanical radial support to maintain patency of the primary lumen 40 and the branch lumen 42 upon implantation. On the other hand, these hoop structures should also provide a minimal desired amount of radial compressibility to prevent damage or undesirable levels of inflammation or irritation of tissue contacting the structure upon implantation. The size, material and configuration of these hoop members may be selected for a particular application and desired point of implantation within a body. For example, these hoop members may be formed by a series of circumferentially connected hexagonal unit cells, as shown in FIGS. 1A and 1B. Alternatively, one or more of the hoop members may be formed as a sinusoidal or zigzag array of alternating struts and bends forming the circumferential hoop perimeter. Other configurations of the hoop members are described below.

Although one example of a support frame 12 is exemplified in FIGS. 1A and 1B with two primary hoop members 20, 22 connected by one longitudinal connecting strut 30 and one branch hoop member 54, other support frame embodiments may include any suitable number of these structures. For example, a support frame may include one, three, four or more primary hoop members longitudinally spaced from each other and connected by any suitable number of longitudinal connecting members. The support frame may also include multiple branch hoop members extending in one, two or more directions from the longitudinal axis. In addition, each branch hoop member may include multiple ring members if desired for a particular application.

The primary hoop members 20, 22 and the branch hoop member(s) 54 may be the same or different in circumference and geometry. For example, the support frame 12 may include a pair of primary hoop members and a branch hoop member of the same or different sizes selected to fit within a body vessel at a point of treatment. Each branch hoop member may be attached to each of the primary hoop members by a self-expanding flexible longitudinal connecting strut to permit the movement of the branch hoop member from the first position within the primary lumen between the primary hoop members to the second position outside the primary lumen by self-expansion of at least one of the primary longitudinal connecting struts. Preferred embodiments of the support frame configurations of the primary hoop members are described below with reference to FIGS. 3 and 4, while alternative support frame configurations are described below, as well. The primary and branch hoop members also can include structural features that facilitate anchoring, such as barbs, and structural features that facilitate visualization, such as radiopaque markers.

Prosthetic Valve Devices

According to FIG. 2A, the prosthesis may be a branched vessel prosthesis 100 preferably including a support frame 112 and a means for regulating fluid through a primary vessel 102 and at least one branch vessel 104 of the body vessel. The primary vessel 102 and the branch vessel 104 can be example vessels found in deep veins, which have been known to bifurcate at one point and reconnect at another point. For example, the branched vessel prosthesis 100 may include one or more valve leaflets positioned and configured to regulate fluid passing through the primary vessel 102 and/or the branch vessel 104. Alternative structures for regulating fluid flow may include a flexible collapsible pocket structure or hinged member within a lumen area, and/or flexible covering material positioned around a portion of the support frame with a portion extending into a lumen and moveable for regulating fluid flow therein.

Preferably, the branched vessel prosthesis devices are configured to treat incompetent or damaged cardiac or venous valves in mammals or to otherwise beneficially modify fluid flow in a bodily passage. For example, a branched vessel prosthesis may be configured to replace or augment the function of natural venous valves operative in veins. The branched vessel prosthesis preferably includes a support frame designed to resist collapsing under the contraction of the muscle present around veins by symmetrically distributing stress and strain within the frame. For venous applications, in particular, blood flow in a vein occurs in an intermittent nature, with surges in antegrade fluid flow occurring between intermittent retrograde fluid flow.

In FIG. 2A, a branched vessel prosthesis 100 preferably provides a one-way valve that permits intermittent blood flow in an antegrade direction 106B while inhibiting, that is reducing or preventing, the retrograde fluid flow in the opposite direction 106A. The branched prosthetic valve 100 is shown in the radially expanded configuration within the branch body vessel. The branched vessel prosthesis 100 includes the support frame 112 that is similar to the support frames 12, described herein. The support frame 112 includes one or more primary hoop members, shown as primary hoop member 120, 122, to define a primary lumen 140 within the primary vessel 102. In this example, the primary hoop members 120, 122 are similar in size as the primary vessel remains substantially similar in size.

The primary hoop members 120, 122 are preferably spaced apart by a longitudinal distance. The distance is sufficient to provide adequate support just distal to the branch vessel 104 and just proximal to the branch vessel 104. Preferably, the distance is also sufficient in order for a branch hoop member 154, described below, to be received within the primary lumen 140 of the primary hoop members 120, 122. The primary hoop members 120, 122 are connected by one or more struts, shown as primary longitudinal connecting struts 130, 131. The struts 130, 131 can be spaced apart circumferentially by a distance sufficient to maintain the patency of the primary vessel 102.

Each of the primary hoop members 120, 122 are connected to the branch hoop member 154 by one or more struts, shown as flexible connecting struts 160, 162. The branch hoop member 154 is positioned within the branch vessel 104 proximate the union with the primary vessel 102. The branch hoop member defines a branch lumen 142 that is in communication with the primary lumen 140.

The branched vessel prosthesis 100 also includes a valve, with a pair of valve leaflets 180 shown, although any number of leaflets can be used. The valve leaflets attach to the support frame 112 and extend from the support frame and across into the primary lumen 140. Preferably, the valve leaflet is attached to the first primary hoop member 120 which is proximal to the second primary hoop member 122, where the terms distal and proximal being relative to the operator. After implantation, the second primary hoop member 122 is generally closer to the heart. Each leaflet 180 includes at least one edge to form a base 181. The base 181 is configured to attach to a primary hoop member 120 of the support frame 112. Attachment of the leaflets to the support frame 112 is described in more detail below. Each leaflet 180 also includes a flexible free edge 182 that is disposed within the primary lumen 140. The flexible free edge 182 portion of the valve leaflets 180 may be moveable between an open position shown in FIG. 2A and a closed position where the opposable free edge portions 182 contact one another. In the open position, the valve leaflets 180 may permit antegrade fluid flow through the primary lumen. In the closed position, the valve leaflets 180 may substantially prevent or reduce fluid flow in a retrograde direction opposite the antegrade direction through the primary lumen. The free edge of the valve leaflet in the open position can be distal to the branch lumen when the branched vessel prosthesis is in the branch radially expanded configuration and the branch hoop member is in the second position. The branch lumen can remain substantially unobstructed by the free edges of each of the valve leaflets when the branch vessel prosthesis is in the radially expanded configuration.

When the branched vessel prosthesis 100 is deployed in a body passageway, such as the primary vessel 102, (e.g., at a treatment site within the venous system), the leaflets 180 move back and forth in response to changes in fluid dynamic pressure. When fluid is flowing through the primary vessel 102 in the normal, antegrade direction 106B back to the heart, the leaflets 180 remain mostly open, moving freely within the primary lumen 140 to permit fluid flow in the antegrade direction 106B. On the other hand, when fluid begins to flow in the retrograde direction 106A away from the heart and opposite its normal, antegrade flow, the leaflets 180 move toward a closed position to prevent fluid flow in the retrograde direction 106A.

In the exemplary branched vessel prosthesis 100 shown, the valve leaflets 180 also regulate fluid flow through the branched vessel 104. For example, the valve leaflets 180 can permit fluid flow in a first direction 107B, while collecting fluid flow in a second opposite direction 107A on the one side of the valve leaflets 180 when in closed configuration. For example, when the body vessel is a deep vein, the first direction 106B and/or 107B may be an antegrade direction of blood toward the heart, while the second direction 106A and/or 107A may be a retrograde direction of blood away from the heart.

Another example of the branched prosthetic valve is shown in FIG. 2B. Here, the primary vessel 102 is bifurcated into two smaller branch vessels 103, 104. The branched prosthetic valve 150 includes the primary hoop member 120 and one or more branch hoop members, shown as branch hoop members 154, 155. One or more flexible connecting members attach to the hoop members together. For example, two primary connecting members 156, 157 extend between the primary hoop member 120 and each of the first and second branch hoop members 154, 155. A flexible connecting member 163 can also connect the two branch hoop members 154, 155. The branch prosthetic valve 150 forms a "Y"-shaped lumen having a primary lumen 141 and two branch lumens 143, 145.

The primary hoop member 120 is shown implanted within the primary vessel 102, while the first and second branch hoop members 154, 155 are shown implanted within the two branch vessels 103, 104. Preferably, the first and second branch hoop members 154, 155 have the same or substantially similar structure. At least one of the first and second branch hoop members 154, 155 is moveable into the primary lumen 140 defined between the primary hoop member 120 and the other of the first and second branch hoop members 154, 155. One or more valve leaflets 180 each can be attached to the primary hoop member 120 to extend into the "Y"-shaped primary lumen 140 to regulate fluid flow within the body vessel. The valve leaflets 180 permit fluid flow in the first antegrade direction 106B along the primary vessel 102 and along the antegrade direction 107B along the branch vessels 103, 104, while substantially preventing fluid flow in retrograde directions 106A, 107A.

With reference to FIG. 2C, another example of the branched vessel prosthesis is shown, depicting a graft material as the means for attaching the branch hoop member to the primary hoop member. Optionally, the graft material can be included in structures with the flexible connecting struts described in other embodiments for better sealing and/or coupling at the intersection of the vessels when vessels movement and sizes are less predictable. The branched vessel prosthesis 185 is similar to the branched vessel prosthesis 100 except the branch hoop member 154 is attached to the primary hoop members 120, 122 by a graft material 186. In other examples, the graft material can be fit within or over the branched vessel prosthesis having the flexible struts connecting the branch hoop member to the primary hoop member(s). The graft material is conformable to a circular or arcuate shape in order to conform to the shape of the primary vessel 102. The graft material 186 is sized to minimize contact with the body vessel wall and to minimize the compression ratio of the primary hoop members in the compressed configuration. The graft material 186 has a length sufficient for securable contact with the primary hoop members, with the illustrated length being to the ends of the hoop members. The graft material 186 also has a fenestration 188, where a second tubular member of graft material 190 is configured to attach to. The graft material 186 and the second graft material 190 may be attached to one another with suturing or other attachment means known in the art. The second graft material 190 has a cross-sectional area sized to fit with the branch vessel 104. The graft material 186 can attach to the primary hoop members 120, 122 and/or the branch hoop member 154 by sutures, bio-adhesives, or other attachment means known in the art. Although the graft materials are shown attached to outside of the respective hoop members, the graft material instead can be attached to the inside of the hoop members, or any combinations thereof.

The graft material 186 can include any suitable biocompatible synthetic and/or biological material, which is suitable for facilitating repair to the injured or diseased blood vessel. The graft material may be non-porous so that leakage from the graft material may be avoided under physiologic forces. The graft material can be made of woven DACRON® polyester (VASCUTEK® Ltd., Renfrewshire, Scotland, UK). The graft material can also be made of any other at least substantially biocompatible material including such materials as other polyester fabrics, polytetrafluoroethylene (PTFE), expanded PTFE, and other synthetic materials known to those of skill in the art. Naturally occurring biomaterials, such as collagen, are also highly desirable, particularly a derived collagen material known as extracellular matrix (ECM), such as small intestinal submucosa (SIS). Other types of xenogenic biomaterials, autologous tissues, and/or allographs, described below in further detail, can also be used.

Figure 3:
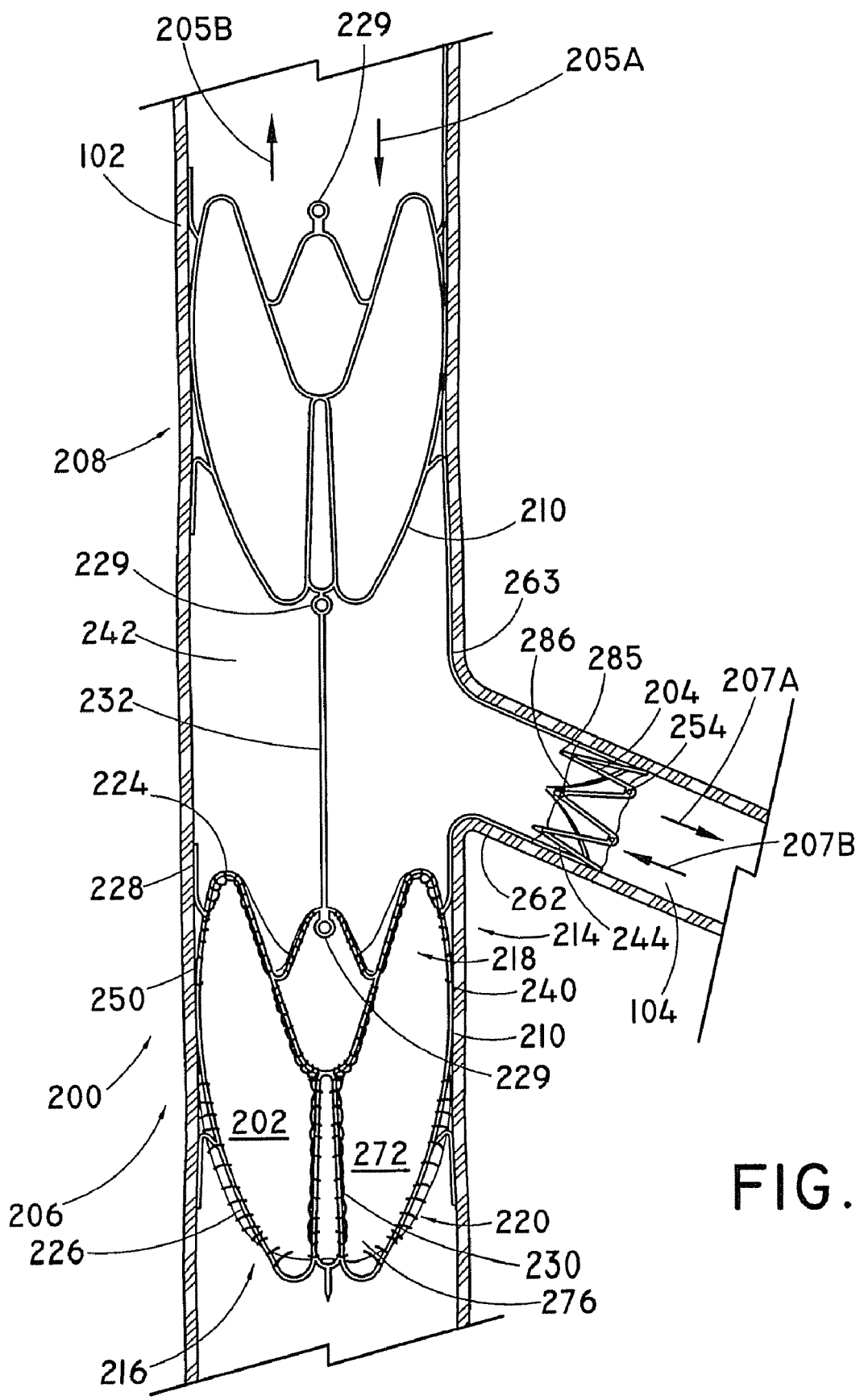
FIG. 3 shows a branched vessel valve prosthesis having a first valve and a second valve within a branched body vessel.

FIG. 3 illustrates another example of the branched vessel prosthesis having valve leaflets attached in the primary hoop member and the branch hoop member. Here, the branch vessel 104 intersects the primary vessel 102. The branched vessel prosthesis 200 includes a pair of valves 202, 204. The first valve 202 of the pair is attached to at least one of the first and second primary hoop members 206, 208 and the second valve 204 is attached to the branch hoop member 254. The first and second primary hoop members 206, 208 can have the same or substantially similar structure.

Figure 4:
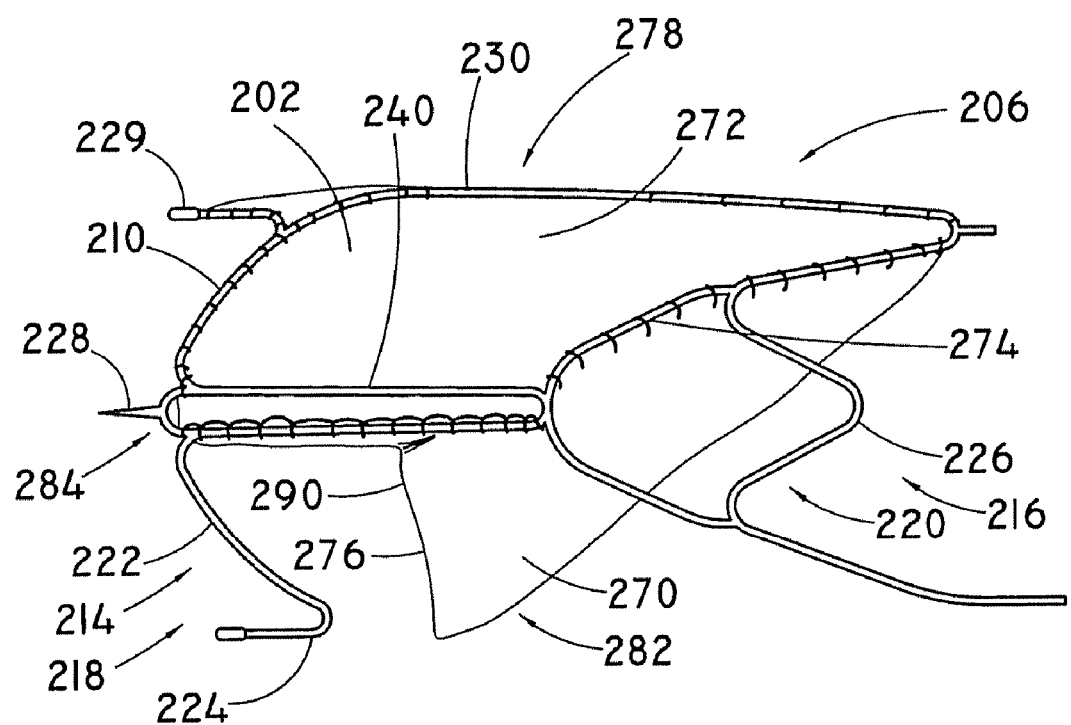
FIG. 4 is a side view of a primary hoop member.

FIG. 4 illustrates in more detail exemplary primary hoop members 206, 208 of the branched vessel prosthesis 200. The primary hoop members 206, 208 include a support frame 210 and at least one primary hoop member includes a valve 202 attached to the support frame 210. Although the primary hoop member in FIG. 4 depicts the support frame with a valve, preferably the primary hoop member 208 does not have a valve.

The support frame 210 is preferably a self-expandable support frame comprising proximal 214 and distal 216 portions connected by various connector segments 230, 240. The proximal portion 214 defines a first serpentine path 218 that extends around the circumference of the support frame 210. The distal portion 216 defines a second serpentine path 220 that also extends around the circumference of the support frame 210. Each serpentine path 218, 220 includes straight strut portions 222 that are interconnected by bends 224. Each serpentine path also includes secondary bends 226 that substantially mirror the bends 224 on the path. The support frame 210 advantageously includes conventional structural features that facilitate anchoring, such as barbs 228, and structural features, such as radiopaque markers 229, that facilitate visualization of the branched vessel prosthesis 200 in conventional or other medical visualization techniques, such as radiography, fluoroscopy, and other techniques. Preferably, radiopaque makers 229 are attached to the support frame and oriented such that the space between the primary hoop members is visual to indicate to the clinician where the branch hoop member is located during delivery, as shown in FIG. 3.

In the illustrated embodiment, each of the connector segments 230, 240 include first and second struts that are substantially straight and disposed substantially parallel to each other. This arrangement of struts in the connector segments 230, 240 is considered advantageous at least because it provides a degree of structural redundancy and gives a secondary attachment point for the valve 202 along the length of the connector segments 230, 240. In embodiments in which the means for attaching the valve leaflet 202 to the support frame 210 extends through only a partial thickness of the tissue of the valve, this secondary attachment point can be used at any point along the length of the segments 230, 240 when a first attempt to pass through a partial thickness of the tissue is unsuccessful. This is particularly advantageous in valve devices in which the valve is attached to the support frame using one or more sutures.

In the illustrated embodiment, one connector segment 230 defines an outwardly-projecting curve. When the branched vessel prosthesis 200 is implanted in a body vessel, the curve forces a part of the vessel wall outward, which defines a sinus at the point of implantation. This structural feature is considered advantageous at least because the provision of a sinus is believed to aid in the opening and closing of the valve 202 by creating flow patterns that facilitate movement of the free edge 276 of the leaflet 270. This may enhance the overall performance of the branched vessel prosthesis. It is believed to be advantageous to attach the contiguous wall portion 272 of the valve 202 to the connector segment 230 defining the outwardly projecting curve. It is believed to be particularly advantageous to form a continuous attachment between the contiguous wall portion 272 and the connector segment 230, such as by suturing along the length of the curve and/or connector segment. This is expected to ensure a more complete definition of the sinus region in the branched vessel prosthesis 200 and to enhance securement of the valve 202 to the support frame 210.

The embodiment illustrated in FIGS. 3 and 4 include a support frame 210 having three connector segments 230, 240, 250. Connector segment 230 defines the curve, as described above, and is disposed substantially opposite to the inside surface of the leaflet 270 of the valve 202. Connector segments 240, 250 are disposed substantially opposite to each other and near the attachment region 274 at which the leaflet 270 is attached to the contiguous wall portion 272. Also, the connector segments 240, 250 may lack the curve of the connector segment 230 and are disposed substantially parallel to each other. This structural arrangement ensures that the valve pocket formed when the valve 202 is in the closed configuration is not shallowly formed and that the leaflet 270 is able to sealingly interact with the vessel wall.

As best illustrated in FIG. 4, the underside 282 of the support frame 210 of primary hoop member 206, which represents the side disposed substantially opposite an exterior surface 278 of the leaflet 270, preferably lacks a connector segment. Instead, this side 282 of the support frame 210 is largely open. This structural arrangement is considered advantageous at least because it enables the free edge 276 of the leaflet 270 to interact with the vessel wall during closure of the valve 202, which is believed to result in better sealing and prevention of fluid flow in the reverse retrograde direction when the valve 202 is in the closed configuration. This configuration is also expected to minimize wear of the leaflet edge 276 because it avoids abrasion that might result if the edge 276 were allowed to interact with a portion of the support frame 210. On the other hand, the underside of the support frame 210 of primary hoop member 208 preferably includes a connector segment (not shown). This side of the support frame 210 of the primary hoop member 208 is enclosed with the connector segments circumferentially spaced.

It is noted that, while the illustrated support frame 210 of primary hoop member 206 includes three connector segments 230, 240, 250, any suitable number can be used and the specific number chosen for a particular valve device according to an embodiment of the invention will depend on various considerations, including the nature and size of the valve 202 and the nature and size of the body vessel into which the valve device is intended to be implanted. Also, while the illustrated connector segments are disposed substantially equidistant from each other, it is noted that any suitable arrangement can be used and the specific arrangement chosen for a particular valve device according to an embodiment of the invention will depend on various considerations, including the nature and size of the valve 202 and the nature and size of the contiguous wall portion 272 of the valve 202.

Referring back to FIG. 3, the primary hoop members 206, 208 are shown implanted within the primary vessel 102, and the branch hoop member 254 is shown implanted within the branch vessel 104. The primary hoop members 206, 208 are connected to one another by one or more longitudinal connecting struts 232, which define a primary lumen 242 within.

The valve 202 is attached to the support frame 210 in a manner such that the valve is normally open, i.e., the free edge 276 of the leaflet 270 is collapsed against the contiguous wall portion. This can allow fluid flow to pass through the lumen 242 of the valve device 200 and the vessel in which it is implanted. As best illustrated in FIG. 4, the valve 202 closes only when a pressure head develops on an antegrade side 284 of the valve 202 that is sufficient to force the free edge 276 of the leaflet 270 away from the contiguous wall portion 272 and adjacent wall of the body vessel and toward, and potentially against, the opposing wall of the body vessel. In this configuration, a valve pocket 290 is formed that fills with fluid until the valve 202 returns to its open configuration, which can occur in response to a change in the fluid pressure differential across the valve 202, a change in fluid flow direction, or both. The first valve 202 permit fluid flow in the first antegrade direction 205B along the primary vessel 102, while preventing fluid flow in the second retrograde direction 205A.

The branch hoop member 254 is preferably connected to both primary hoop members 206, 208 by flexible connecting members 262, 263 as illustrated. However, the branch hoop member may be connected to only one of the primary hoop members by one or more flexible connecting members, by sutures, or by graft materials, as described above. The branch hoop member 254 defines a branch lumen 244 that is in communication with the primary lumen 242. The branch hoop member 254 can have any of the frame structures described or shown in the specification. The valve 204 can be any of the valve configurations described or shown in the specification.

The branched vessel prosthesis 200 may be used to prevent fluid flow from the primary lumen 242 into the branch lumen 244 and/or from the branch lumen into the primary lumen. The branch valve 204 is attached to the branch hoop member 254 in a manner such that the valve is normally open, i.e., the free edge 286 of the leaflet 285 is collapsed against the contiguous wall portion. This can allow fluid flow to pass through the branch lumen 244 of the valve device 200 and the vessel in which it is implanted. The valve 204 closes only when a pressure head develops on a side of the valve 204 that is sufficient to force the free edge 286 of the leaflet 285 away from the contiguous wall portion and adjacent wall of the body vessel and toward, and potentially against, the opposing wall of the body vessel for monocusp valves or other valve leaflets for multi-leaflet valves. The valve 204 returns to its open configuration, which can occur in response to a change in the fluid pressure differential across the valve 204, a change in fluid flow direction, or both. The second valve 204 permits fluid flow in the second antegrade direction 207B along the branched vessel 104, into the primary lumen 242, while substantially preventing fluid flow in retrograde directions 207B. It is appreciated that it may be desirable to reorient the branch valve 204 in order to work oppositely, i.e., to prevent flow in the antegrade direction, while allowing fluid flow in the retrograde direction.

Support Frames

The support frames described above, or any portion thereof, may be self-expanding, or alternatively, may be forcibly expandable (e.g., balloon-expandable). The support frame may be formed from any suitable material. Preferred materials for frames include those materials that can provide the desired functional characteristics with respect to mechanical load bearing, biological compatibility, modulus of elasticity, radio-opacity, or other desired properties. For some examples, the materials used to form the implantable frames can comprise a material that exhibits excellent corrosion resistance. For some examples, the material can be selected to be sufficiently radiopaque and create minimal artifacts during magnetic resonance imaging techniques (MRI). In some examples, the implantable frame can comprise a metal, a metal alloy, a polymer, or any suitable combination thereof, for example as frame with multiple layers.

Preferably, the support frames are self-expanding comprising a material capable of significant recoverable strain to assume a low profile for delivery to a desired location within a body lumen. After release of the compressed self-expanding stent, it is preferred that the frame be capable of radially expanding back to its original diameter or close to its original diameter. Accordingly, some examples provide frames made from material with a low yield stress (to make the frame deformable at manageable balloon pressures), high elastic modulus (for minimal recoil), and is work hardened through expansion for high strength. Particularly preferred materials for self-expanding implantable frames are shape memory alloys that exhibit superelastic behavior, i.e., are capable of significant distortion without plastic deformation. Frames manufactured of such materials may be significantly compressed without permanent plastic deformation, i.e., they are compressed such that the maximum strain level in the stent is below the recoverable strain limit of the material. Discussions relating to nickel titanium alloys and other alloys that exhibit behaviors suitable for frames can be found in, e.g., U.S. Pat. No. 5,597,378 to Jervis and PCT Publication WO 95/31945 (Burmeister et al.), each of which is hereby incorporated by reference in its entirety. A preferred shape memory alloy is Ni—Ti, although any of the other known shape memory alloys may be used as well. Such other alloys include: Au—Cd, Cu—Zn, In—Ti, Cu—Zn—Al, Ti—Nb, Au—Cu—Zn, Cu—Zn—Sn, CuZn—Si, Cu—Al—Ni, Ag—Cd, Cu—Sn, Cu—Zn—Ga, Ni—Al, Fe—Pt, U—Nb, Ti—Pd—Ni, Fe—Mn—Si, and the like. These alloys may also be doped with small amounts of other elements for various property modifications as may be desired and as is known in the art. Nickel titanium alloys suitable for use in manufacturing implantable frames can be obtained from, e.g., Memry Corp., Bethel, Conn. One suitable material possessing desirable characteristics for self-expansion is Nitinol, a Nickel-Titanium alloy that can recover elastic deformations of up to 10 percent. This unusually large elastic range is commonly known as superelasticity. Optionally, the material can be various types of spring metals.

In particular, when the flexible connecting struts connecting the branch hoop member to the primary hoop members are made of nickel titanium alloys or other heat-settable materials, the flexible connecting struts can be heat set to assume the second positions. Accordingly, it is to be understood that the various lengths of the flexible connecting struts and the angles between the branch hoop member and the primary hoop members can be achieved.

Alternatively, the implantable frames are designed to be expanded by a balloon or some other device (i.e., the frames are not self-expanding), and may be manufactured from an inert, biocompatible material with high corrosion resistance that can be plastically deformed at low-moderate stress levels, such as tantalum. The implantable frames can be deployed by both assisted (mechanical) expansion, e.g. balloon expansion, and self-expansion means. In examples where the implantable frame is deployed by mechanical (balloon) expansion, the implantable frame is made from materials that can be plastically deformed through the expansion of a mechanical assist device, such as by the inflation of a catheter based balloon. When the balloon is deflated, the frame can remain substantially in the expanded shape. Other acceptable materials include stainless steel, titanium ASTM F63-83 Grade 1, niobium or high carat gold K 19-22. One widely used material for balloon expandable structures is stainless steel, particularly 304 and 316L stainless steel. This material is particularly corrosion resistant with a low carbon content and additions of molybdenum and niobium. Fully annealed, stainless steel is easily deformable. Alternative materials for mechanically expandable structural frames that maintain similar characteristics to stainless steel include tantalum, platinum alloys, niobium alloys, and cobalt alloys.

Optionally, the support frame may be formed from or coated with other materials, such as polymers and bioabsorbable polymers may be included in or on the implantable support frames. The support frames or portions thereof can optionally comprise material that permits identification of the position or orientation of the frame within a body passage. Radiopaque markers are advantageously positioned at one or more ends of the implantable frame to aid the physician in positioning the frame at a site inside a body vessel. For example, portions of the implantable frame can include a radiopaque material that can be identified by X-rays. For example, U.S. Pat. No. 6,409,752 to Boatman et al., incorporated herein by reference in its entirety, discloses various radiopaque materials that can be used in or on the implantable frames.

The implantable frames may be fabricated using any suitable method known in the art. Preferably, the complete frame structure, including the primary and branch hoop members and the respective connecting struts, is cut from a solid tube or sheet of material, and thus the frame would be considered a monolithic unit. Laser cutting, water-jet cutting and photochemical etching are all methods that can be employed to form the structural frame from sheet and tube stock. Still other methods for fabricating the complete frame structure as previously disclosed would be understood by one of skill in the art.

Alternatively, the frame can also be formed from wire using wire forming techniques, such as coiling, braiding, or knitting. By welding the wire at specific locations a closed-cell structure may be created. This allows for continuous production, i.e. the components of the implantable frame may be cut to length from a long wire mesh tube. In addition, an implantable frame is constructed from sheet, wire (round or flat) or tubing. The method of fabrication can be selected by one skilled in the art depending on the raw material used. Techniques for forming implantable frames are discussed, for example, in Dougal et al., "Stent Design: Implications for Restenosis," Rev. Cardiovasc Med. 3 (suppl. 5), S16-S22 (2002), which is incorporated herein by reference in its entirety.

Examples of suitable support frames for use in medical devices according to the invention include those described in U.S. Pat. No. 6,464,720 to Boatman et al.; U.S. Pat. No. 6,231,598 to Berry et al.; U.S. Pat. No. 6,299,635 to Frantzen; U.S. Pat. No. 4,580,568 to Gianturco; and U.S. published applications 2001/0039450A1 to Pavcnik et al.; 2004/0260389A1 to Case et al.; 2007/0038291A1 to Case et al.; 2007/0162103A1 to Case et al.; 2007/0100435A1 to Case et al.; and 2007/0021826 to Case et al.; each of which is hereby incorporated by reference in its entirety for the purpose of describing suitable support frames for use in medical devices according to the invention. Another example is a Zilver® stent manufactured by Cook, Inc of Bloomington, Ind.

A support frame can optionally be sterilized using any suitable technique known in the art, or equivalents thereto. For example, an implantable frame can be sterilized using ethylene oxide sterilization, as described in AAM/ISO 11135:1994 "Medical Devices—Validation and Routine Control of Ethylene Oxide Sterilization," incorporated herein by reference in its entirety. In some examples, a sterilized implantable frame satisfies a minimum Sterility Assurance Level (SAL) of about $10^{-6}$.

Valve Leaflets

A wide variety of materials acceptable for use as a valve member or valve leaflet are known in the art, and any suitable material can be utilized. The material chosen need only be able to perform as described herein, and be biocompatible, or able to be made biocompatible. Examples of suitable materials include natural materials, and synthetic materials.

It is noted that, although the embodiments illustrated include a single leaflet or two leaflet design, it is expressly understood that a valve having two or more leaflets can be used in the valve devices according to the invention. For example, for valve devices intended to be used in body vessels having relatively large internal diameters (e.g., vessels with diameters greater than 16 mm, such as adult human jugular and iliac veins), it may be advantageous to use a valve that includes two or more leaflets attached to a contiguous wall portion. In these embodiments, the contiguous wall portion need not include any commissure(s) between the leaflets. Multi-leaflet valves are advantageously attached to the support frame such that the free edges of the leaflets are able to coapt with each other such that the leaflets can close a valve opening formed inside the lumen of the valve device.

In certain examples of the disclosure, the leaflet is formed from a flexible material comprising a naturally derived or synthetic collagenous material, and especially an extracellular collagen matrix material. Examples of suitable natural materials include collagen and extracellular matrix (ECM) material, such as submucosa. The "extracellular matrix" is typically a collagen-rich substance that is found in between cells in animal tissue and serves as a structural element in tissues. Such an extracellular matrix is preferably a complex mixture of polysaccharides and proteins secreted by cells. The extracellular matrix can be isolated and treated in a variety of ways. Following isolation and treatment, it is referred to as an ECM. ECM may be isolated from submucosa (including small intestine submucosa), stomach submucosa, urinary bladder submucosa, tissue mucosa, renal capsule, dura mater, liver basement membrane, pericardium, serosa, and peritoneum or other tissues. One specific example of ECM is small intestine submucose (SIS). When implanted, SIS can undergo remodeling and can induce the growth of endogenous tissues upon implantation into a host. SIS has been used successfully in vascular grafts, urinary bladder and hernia repair, replacement and repair of tendons and ligaments, and dermal grafts. SIS is particularly well-suited for use as valve members, such as leaflets. These layers may be isolated and used as intact natural sheet forms, or reconstituted collagen layers including collagen derived from these materials or other collagenous materials may be used. For additional information as to submucosa materials useful in the present disclosure, and their isolation and treatment, reference can be made to U.S. Pat. Nos. 4,902,508, 5,554,389, 5,993,844, 6,206,931, and 6,099,567, the contents of which are incorporated herein by reference in their entirety. Renal capsule tissue can also be obtained from warm blooded vertebrates, as described more particularly in copending U.S. patent application Ser. No. 10/186,150, filed Jun. 28, 2002, and PCT Publication WO/03002165, the contents of which are incorporated herein by reference in their entirety. In one example of the disclosure, the ECM material is porcine SIS. SIS can be prepared according to the method disclosed in U.S. 2004/0180042A1, the contents of which are incorporated herein by reference in its entirety. In addition to xenogenic biomaterials, such as SIS, autologous tissue can be harvested as well. Additionally Elastin or Elastin Like Polypeptides (ELPs) and the like offer potential as a material to fabricate the flexible covering or discrete shaping members to form a device with exceptional biocompatibility. Another alternative is use of allographs such as harvested native valve tissue. Such tissue is commercially available in a cryopreserved state.

The valve leaflet may be formed from a synthetic polymeric material. Examples of suitable polymeric materials include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, the valve leaflet material may be a biocompatible polyurethane or derivative thereof. One example of a biocompatible polyurethane is THORALON (THORATEC, Pleasanton, Calif.), as described in U.S. Pat. Application Publication No. 2002/0065552 A1 and U.S. Pat. No. 4,675,361, both of which are incorporated herein by reference. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances.

In one exemplary method, the fabrication is done in accordance with the method described in incorporated U.S. Non-provisional patent application Ser. No. 12/252,253, which is incorporated herein by reference in its entirety. In this method, a xenogeneic valve is harvested and fixed using suitable techniques, such as by fixing the valve with gluteraldehyde or any other suitable cross-linking agent. Examples of suitable fixation techniques are described in U.S. Pat. No. 4,800,603 to Jaffe; U.S. Pat. No. 5,595,571 to Jaffe and Hancock; U.S. Pat. No. 5,720,777 to Jaffe and Hancock; U.S. Pat. No. 5,843,180 to Jaffe and Hancock; and U.S. Pat. No. 5,843,181 to Jaffe and Hancock, each of which is hereby incorporated by reference in its entirety for the purpose of describing suitable techniques for fixing a xenogeneic valve for inclusion in a valve device according to the disclosure.

A second step of the exemplary method of making valve devices suitable for implantation in a patient comprises attaching the valve to a support frame. In exemplary methods, the step attaching the valve to a support frame is accomplished by connecting the valve to the support frame using a single suture.

Alternatively, the valve leaflet may be formed on the support structure by an appropriate means, including but not limited to vapor deposition, spraying, electrostatic deposition, ultrasonic deposition, or dipping. One or more valve leaflets can be attached to the support frame by other methods. In one example, a sheet of material is cut to form a valve leaflet and the edges of the leaflet are wrapped around portions of a support frame and portions of the valve leaflet sealably connected together to fasten the valve leaflet around the support frame. For example, one edge of a sheet of valve leaflet material can be wrapped around a portion of the support frame and held against the body of the valve leaflet, so that the valve leaflet material forms a lumen enclosing a portion of the support frame. A small amount of a suitable solvent is then applied to the edge of the valve leaflet material to dissolve the edge into an adjacent portion of the valve leaflet material and thereby seal the material around the support frame.

In another example, the sheet of valve leaflet material is shaped to form the valve leaflet that is attached to a portion of a support frame using stitching through the valve leaflet material and around a portion of the support structure, adhesives, tissue welding or cross linking to directly join the valve leaflet material to the support frame. A valve leaflet attached to a support frame can be permitted to move relative to the support frame, or the valve leaflet can be substantially fixed in its position or orientation with respect to the support frame by using attachment configurations that resist relative movement of the valve leaflet and the support frame. Examples of other implantable valves, and their preparation, for inclusion in devices according to the invention include U.S. patent application Ser. No. 12/252,253, filed on Oct. 15, 2008, entitled "Biological Valve for Venous Valve Insufficiency," and U.S. patent application Ser. No. 12/252,918, filed on Oct. 16, 2008, entitled "Implantable Valve Device," each of which is hereby incorporated by reference in its entirety.

Delivery System

In a second embodiment, intraluminal prosthesis delivery systems are provided. Preferably, the delivery system includes a catheter and one embodiment of the branched prosthetic valve or frames described above.

For example, the various embodiments of the branched vessel prosthesis can be compressed to the radially compressed configuration, as described with reference to FIGS. 1A and 1B. The branched vessel prosthesis is compressed within the primary lumen defined by the compressed primary hoop members and enclosed by a retaining sheath at or near the distal end of a delivery catheter. Within a body vessel at a point of treatment, the branched vessel prosthesis can be expanded, for example, by removing the retaining sheath, or portion thereof, and/or inflating a balloon from inside the branch vessel prosthesis to radially expand one or more primary hoop members. In addition, with the branch hoop member within the primary lumen, the delivery system may include a means for retaining and/or releasing the branch hoop member. The delivery configuration can be maintained prior to deployment of the branch vessel prosthesis by any suitable means, including a sheath, a suture, a tube or other restraining material around all or part of the compressed branch vessel prosthesis, or by other methods.

Figure 5A:
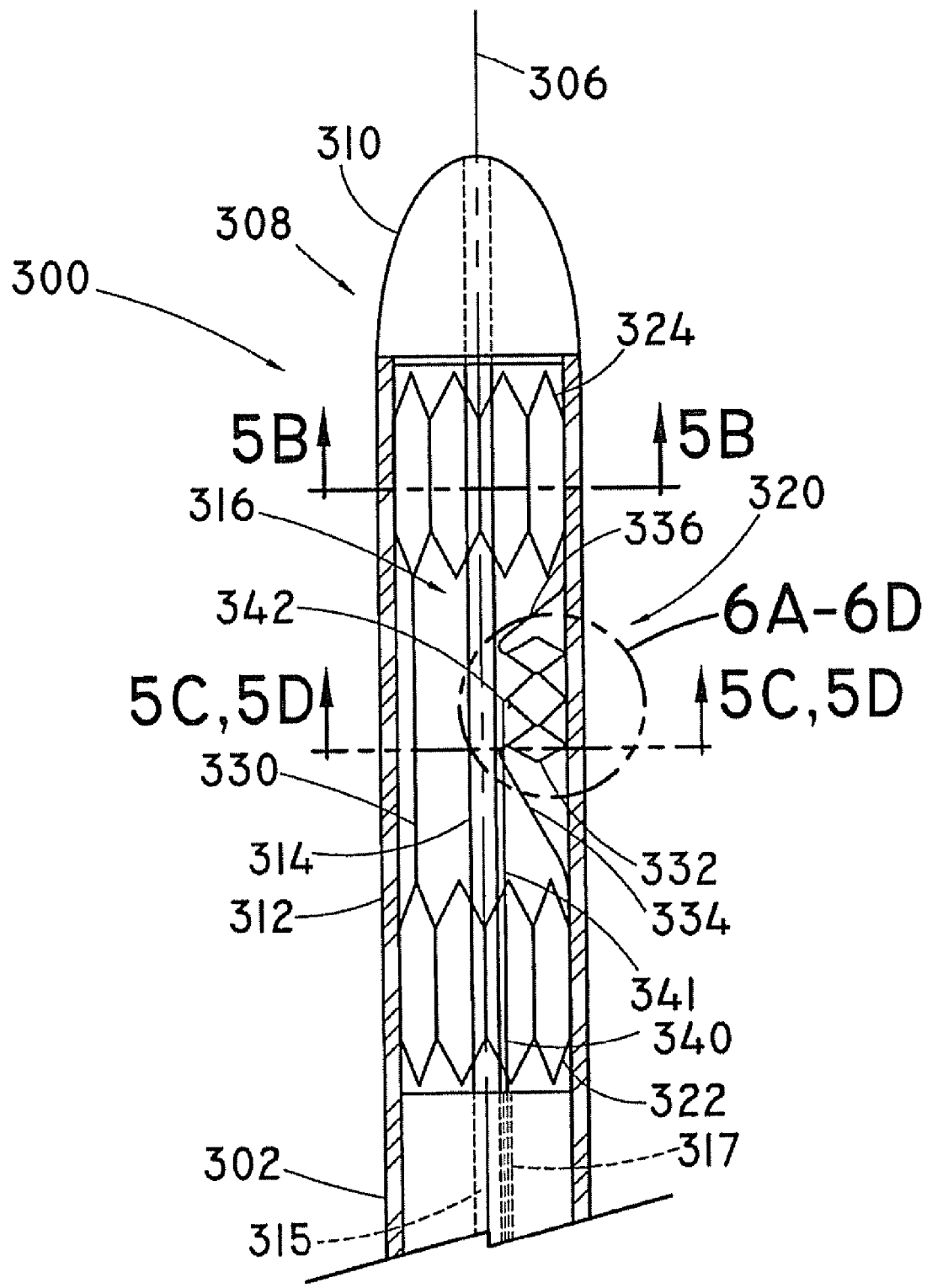
FIG. 5A shows a cutaway view of the distal end of a delivery system with a loaded branched vessel prosthesis.
Figure 5B:
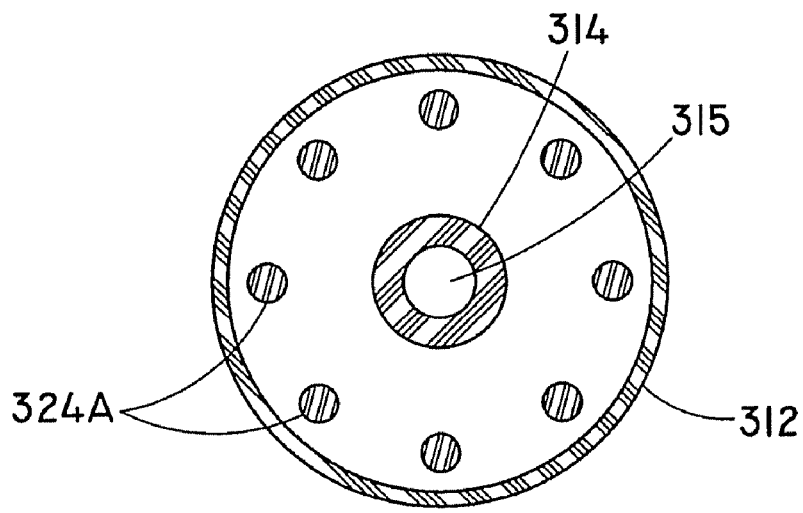
FIG. 5B is a cross sectional view of the delivery system taken along line 5A-5A of FIG. 5A.
Figure 5C:
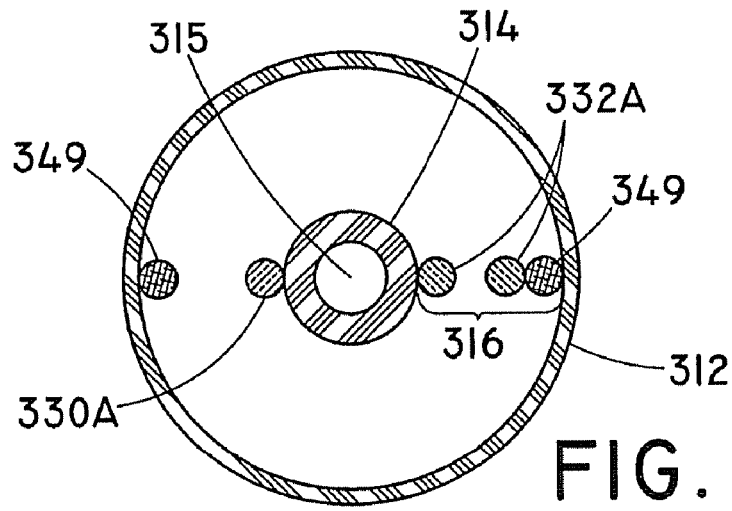
FIG. 5C is a cross sectional view of the delivery system taken along line 5B-5B of FIG. 5A.
Figure 5D:
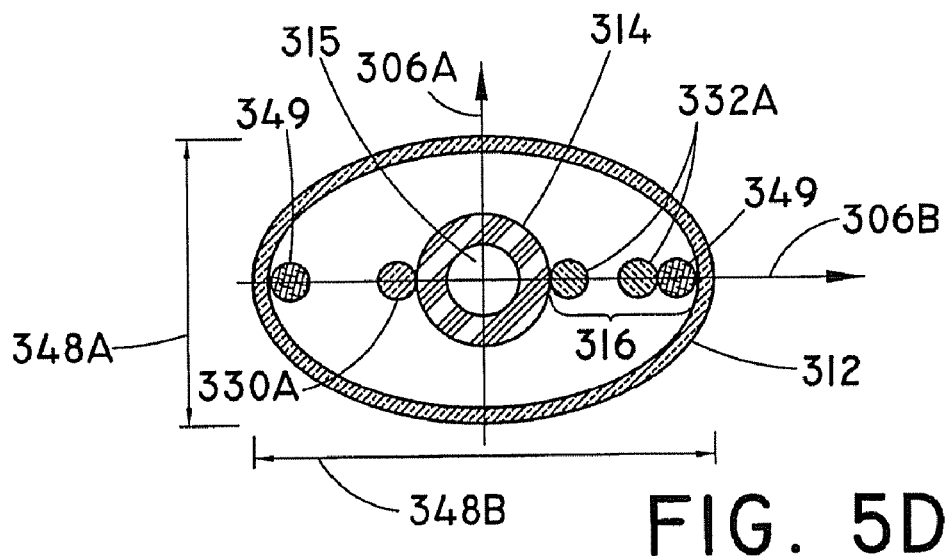
FIG. 5D is a cross sectional view of a delivery system having an elliptical cross-section.

FIGS. 5A-5C show a portion a delivery system 300, showing the distal end of a delivery catheter 302 having a longitudinal axis 306 extending from a proximal end (not shown) to a tapered tip 308 at the distal end 310. The delivery catheter 302 includes an outer sheath 312 enclosing an inner shaft 314 defining a wire guide lumen. The inner shaft 314 may have an additional channel 317 for receiving a wire member of a tether system or trigger wire system, as describe below. The outer sheath 312 is translatable along the longitudinal axis 306 relative to the inner shaft 314. A branched vessel prosthesis 320 in a radially compressed configuration is disposed in a space 316 defined between a portion of the inner shaft 314 and the outer sheath 312, as shown in FIGS. 5C-D.

The branched vessel prosthesis 320 may have any configuration described with respect to the embodiments described above. For example, the branch vessel prosthesis 320 includes a pair of longitudinally spaced primary hoop members 322, 324 in a radially compressed configuration within the outer sheath 312 about the inner shaft 314. The primary hoop members 322, 324 are joined by one or more primary longitudinal connecting struts 330.

The branched vessel prosthesis 320 also includes a branch hoop member 332 positionable in a first position between the pair of primary hoop members 322, 324. The branch hoop member 322 can be connected by one or more flexible connecting members, shown as 332, 336, suture or graft materials. When the branch hoop member is in the first position, the branch hoop member is positioned between the surfaces of the outer sheath 312 and the inner shaft 314, but not coaxially around the inner shaft 174.

Figure 6A:
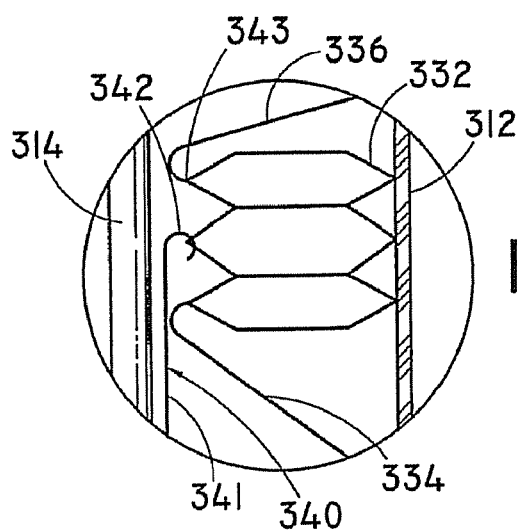
FIGS. 6A-6D are close-up views of a means for retaining the branch hoop member in the first position.

The delivery system 300 also includes a means for retaining the branch hoop member 332 in the first position. For example, with reference to FIG. 6A, the retaining means may include a mechanical tether 340. The mechanical tether 340 includes a control member 341, such as a wire or tube, extending from the proximal portion of the delivery catheter (not shown) to a distal hook portion 342. The hook portion 342 is configured to receive one or more proximal apices 343 (or distal apices) of the struts of the branch hoop member 332. When the mechanical tether 340 is coupled to the proximal apices 343, the mechanical tether 340 can be put under tension and locked by conventional means at the proximal portion in order to fix the branch hoop member 332 to the first position. After unlocking the proximal portion, the proximal end of the mechanical tether 340 can be manipulated such that the hook portion 342 is removed from attachment with the proximal apices 343 to free the branch hoop member 332, thereby allowing the branch hoop member to move freely from the first position to the second position. The hook portion 342 can be removed from attachment by sliding the mechanical tether in the distal direction until the hook portion 342 is removed from contact with the proximal apices 343. The radial expansion of the primary hoop members 322, 324 can be performed independently from the transverse extension of the branch hoop member 332 away from the longitudinal axis 306. In addition, the apices or apertures of the branch hoop member can have a loop to bring the respective apices together as described below.

Figure 6B:
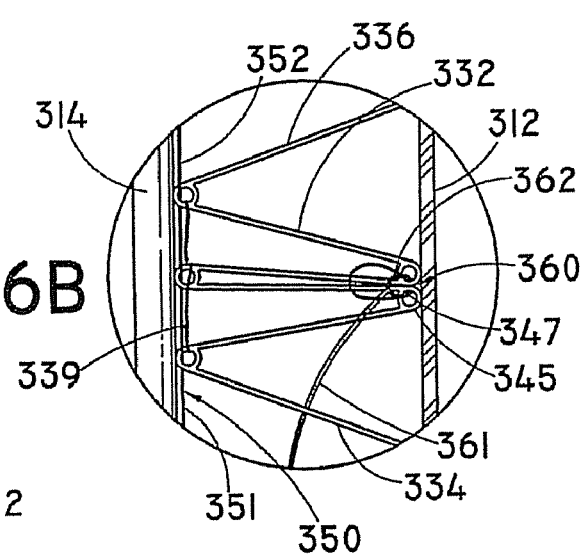
Figure 6C:
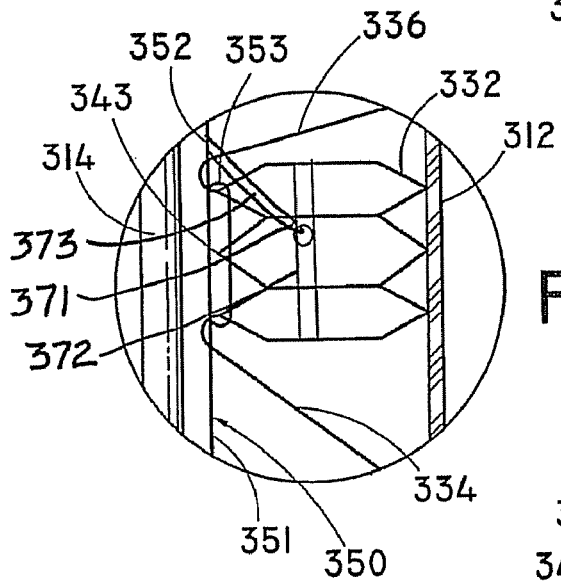
Figure 6D:
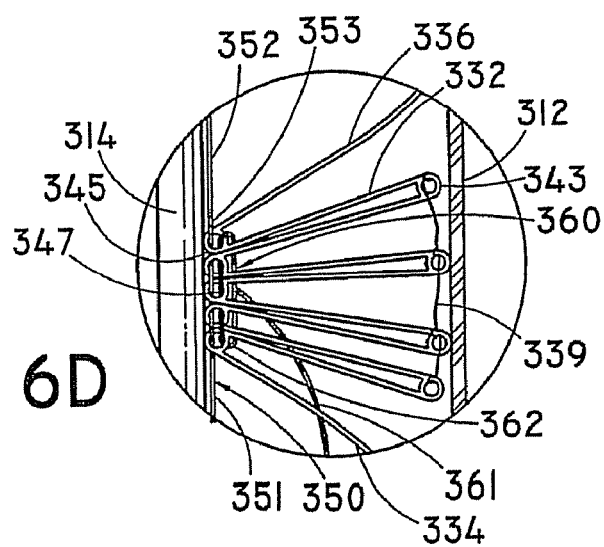

With reference to FIGS. 6B-6D, the retaining means may include a trigger wire system 350 including a control member 351, such as a wire or tube, and a distal portion 352 coupled to the apices or apertures of the struts of the branch hoop member 332. The control member 351 can have a distal end that is removably attached to the tapered tip 308. As shown in FIG. 6B, the distal portion 352 can be inserted through at least one apex in order to retain the branch hoop member 332, shown as a zigzag stent, within the first position. The branch hoop member shown in all of the figures may have apertures for receiving a suture 339 (proximal) or 347 (distal) disposed at one or more of the apices. The suture can be attached to the apices or the apertures, proximal and/or distal, by wrapping around or tying a knot in order to maintain a circular or elliptical shape while the branch hoop member radially expands in the second position. The control member 351 can be removed from contact with the apices or apertures by conventional means.

Optionally, the distal apices 345 may also includes a second retaining means 360, as shown in FIGS. 6B and 6D, including a retaining ring 362 running through at least one apex or aperture to draw or gather the apices together in order to retain and/or maintain the branch hoop member in the radially compress configuration, especially after moving to the second position. The retaining ring 362 is preferably a ring of semi-rigid to rigid biocompatible material having ends that overlap sufficiently to provide retention force to keep the apices together and to permit removal of the ring from the apices. At least a portion of the retaining ring 362 may also be tapered in order to provide more strength to the ring where the control member attaches and less strength at the overlap for easier removal. After the branch hoop member is released to the second position, the retaining ring 362 can be removed from the apices in order for the apices of the branch hoop member to radially expand against the vessel. The retaining ring 362 can be attached to a second trigger wire system via a connecting member 361 so that retraction of the control member of the second trigger wire system up to a certain point removes the retaining loop 362 from contact with the apices 345. This can allow the branch hoop member to move to the second position. Optionally, the retaining ring can be independently removed from contact with the branch hoop member integrally with the removal of the control member of the trigger wire system 350. The coupling of the retaining ring to the apices and the rigidity of the connecting member 361 may be sufficiently strong in order to urge the branch hoop member into the branch vessel if there are issues in deploying and/or urge the branch hoop member back into position between the primary hoop members for repositioning.

As shown in FIG. 6C, the distal portion 352 of the trigger wire may includes a loop 353 running through at least one apex that is coupled to the control member 351. Accordingly, removal of the control member 351 urges the loop to decouple from the branch hoop member. FIG. 6D illustrates another means for retaining. Instead of attaching to the proximal apices 343 as described in FIGS. 6B and 6C, the distal portion 353 of the control member or loop is attached to the distal apices 345. The distal apices 345 may also include the retaining ring 362 running through at least one apex or aperture to draw or gather the apices together in order to retain and/or compress the branch hoop member after being inverted, as shown in FIG. 6D. In this instance, the flexible strut members 334, 336 remain against the sheath. When the control member 351 is released, the distal apices 345 unfold or evert to assume the second position of the branch hoop member 332 with the distal portion still collected inward. The connecting member 361 can be manipulated in order to urge the distal apices 345 to unfold. Once the distal apices 345 are within the branch vessel, the connecting member 361 can again be manipulated to decouple from the distal apices 345 in order for the distal apices to radially expand-within the branch vessel. It is appreciated that any combination of retaining means can be used, such as a mechanical tether, a trigger wire system, and/or second retaining means, as described above, such as a mechanical tether attached to the distal apices. One example of a loop system is described in U.S. Pat. No. 6,695,875, which is hereby incorporated by reference in its entirety.

Alternatively, as shown in FIG. 6C, a plurality of loops attached to the branch hoop member and coupled to the retaining means can be configured to radially compress the branch hoop member. For example, a first loop 371 can be wrapped around the branch hoop member 332 in a first direction to radially compress the branch hoop member to a smaller diameter, and a second loop 372 can be wrapped around in a second direction opposite the first. Where the ends of the first and second loops meet, a loop 373 or control member can be inserted therein to maintain the radially compressed configuration of the branch hoop member 332. The loop 373 having a length for permitting movement of the branch hoop member to the second position. Removal of the loop 373 or control member from the end of the loops 371, 372 causes the branch hoop member 332 to radially expand. The removal of the loop 373 is advantageous after the branch hoop member is in the second position. A second trigger wire system can be used to remove the loop. Similar arrangements of loops to compress or reduce the diameter of the branch hoop member are described in U.S. Publs. 2007/0043425A1 and 2008/0294234, which are incorporated herein by reference in their entirety.

For delivery of the branched vessel prosthesis, the delivery system 300 can have a circular cross section for orienting and deploying the branch hoop member 332. The delivery catheter 302, or a portion thereof, can also have a circular cross section perpendicular to the longitudinal axis 306. For example, the outer sheath 312 may have a circular cross section, as shown in FIGS. 5B and 5C. FIG. 5B shows the cross section of the delivery system of FIG. 5A along line 5B-5B, while FIG. 5C shows the cross section of the delivery system of FIG. 5A along line 5C-5C. The outer sheath 312 encloses the inner shaft 314, which defines a wire guide lumen 315. The inner shaft 314 can have an elliptical cross section, but may have any suitable shape. The wire guide lumen 315 is preferably circular and sized to slidably enclose a suitable wire guide.

In FIG. 5B, a series of strut cross sections 324A of the primary hoop member 324 are disposed around the inner shaft 314. In other embodiments, the delivery system, the outer sheath and/or the inner shaft may have an elliptical cross-section, as shown in FIG. 5D, but could be oblong, oval, egg-shaped or the like. For example, the elliptical cross-section of the outer sheath 312 has a first distance 348A in a first direction 306A (minor axis) and a second distance 348B in a second direction 306B (major axis) perpendicular to the first direction. The first and second directions 306A, 306B are perpendicular to the longitudinal axis 306. The second distance 348B is greater than the first distance 348A. FIG. 5C illustrates a cross section 330A of the primary longitudinal connecting strut and two cross sections 332A of the branch hoop member 332 that are disposed between the inner shaft 314 and the outer sheath 312. In elliptical applications, the branch hoop member in the first position is preferably positioned along the second radial direction (major axis) to take advantage of the additional distance provided by the second distance.

The positioning and delivery of the branch hoop member 332 within a body vessel may be performed easier with radiopaque marker strips 349, as shown in FIG. 5C, although other types of imagable means known in the art may be used. The strips 349 are positioned along the interior surface of the outer sheath 312 or exterior surface of the inner shaft 314. The strips 349 can be strategically placed such that rotating the delivery catheter around the longitudinal axis 306 changes the apparent width of the outer sheath 312 in a two-dimensional planar representation of the delivery catheter, such as an x-ray or fluoroscopic image. For example, two strips 349 can be placed at diametrically opposite ends. By maximizing the apparent width of the outer sheath 312 enclosing the branched vessel prosthesis 320 at a branched vessel site, the direction of deployment of the branch hoop member 332 can be oriented prior to deployment of the branch hoop member 332. Further, for elliptical applications the strips 349 can be positioned along the interior wall of the outer sheath at the intersection between the major axis and/or minor axis and the outer sheath to further enhance the detection of the orientation of the branch hoop member.

Methods of Delivery and Treatment

In a third embodiment, methods of delivering a branched vessel prosthesis to a branched vessel site are provided. The branched vessel device is preferably delivered from a percutaneous catheter according to the second embodiment. The branched vessel prosthesis may include a valve, as described above. The branched vessel prosthesis is preferably adapted for transcatheter percutaneous delivery. The branched vessel prosthesis can be moveable from a compressed delivery state suitable for introduction to a point of treatment with a catheter delivery system, to a radially expanded implanted state for retention within the body vessel at the point of treatment therein.

Branched vessel prosthesis can be deployed in a body lumen by means appropriate to their design. For example, the branched vessel prosthesis can be adapted for deployment using conventional methods known in the art and employing percutaneous transluminal catheter devices. The branched vessel prosthesis is designed for deployment by any of a variety of in situ expansion means. The branched vessel prosthesis may be mounted onto a delivery catheter that holds the branched vessel prosthesis as it is delivered through the body lumen. The branched vessel prosthesis may then be translated through a body to a point of treatment by advancing the catheter over a wire guide to the location of the point of treatment. The branched vessel prosthesis can be released and allowed to self-expand into contact with the body vessel wall. The prosthesis can be released by withdrawing an outer sheath from over the branched vessel prosthesis. The branched vessel prosthesis may be deployed by radial expansion of the primary hoop member(s) within a primary vessel and extension of the branch hoop member(s) into a branch vessel at the point of treatment. The catheter, sleeve, and guidewire may then be removed from the patient. This deployment is effected after the branched vessel prosthesis has been introduced percutaneously, transported transluminally and positioned at a desired location by means of the catheter.

The system may be configured to retain a branched vessel prosthesis in the radially compressed configuration with the branch hoop member positioned between the pair of radially compressed primary hoop members. Preferably, the system is adapted to permit expansion of individual primary hoop members and lateral extension of the branch hoop member independent of each other. For example, the delivery system may include a delivery catheter with a distal portion adapted to receive and retain the branched vessel prosthesis in the radially compressed configuration.

Figure 7A:
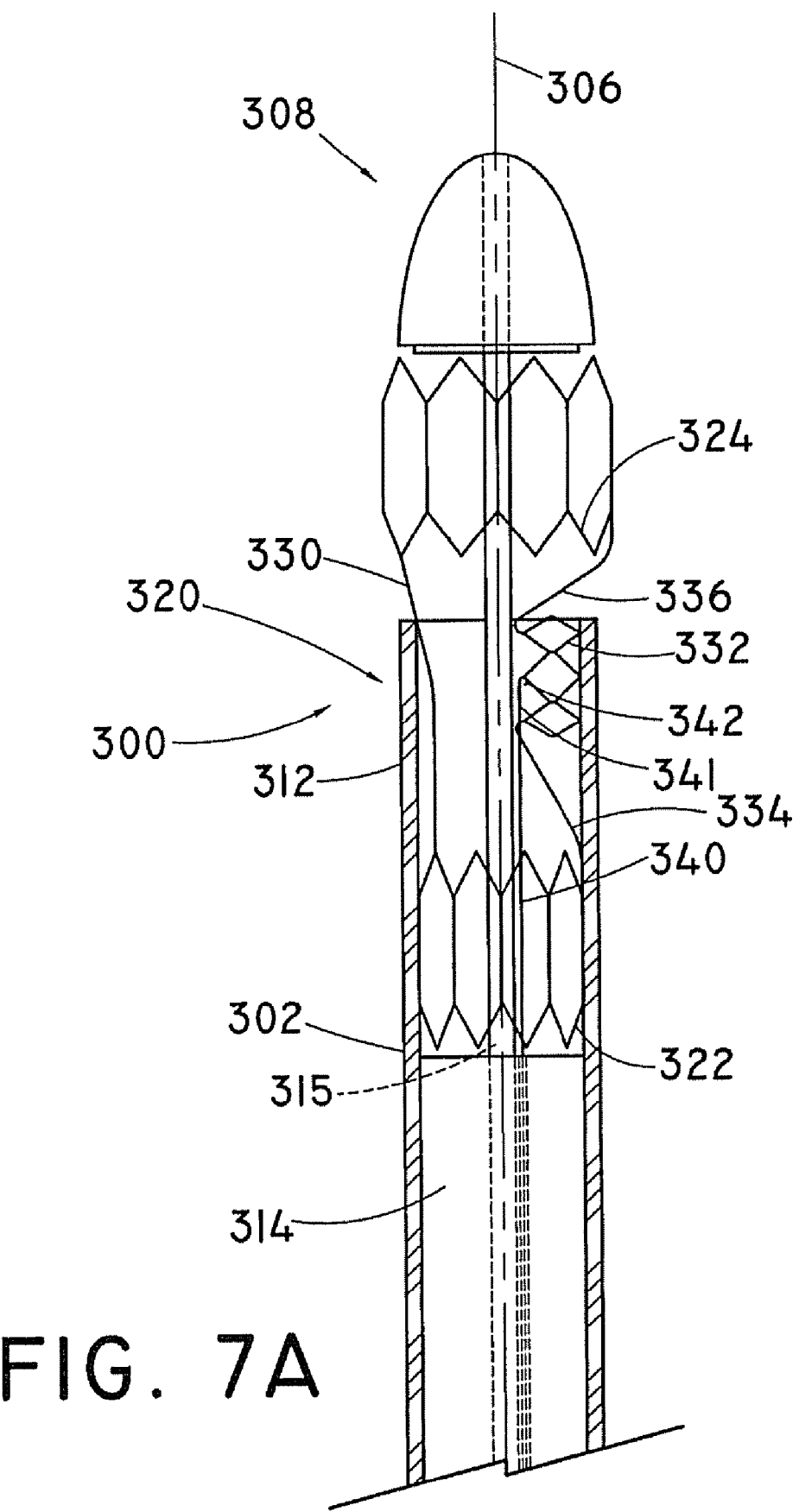
FIGS. 7A-7C are cutaway views of a portion of the delivery system in FIG. 5A depicting a method of delivery of a branched vessel prosthesis.
Figure 7B:
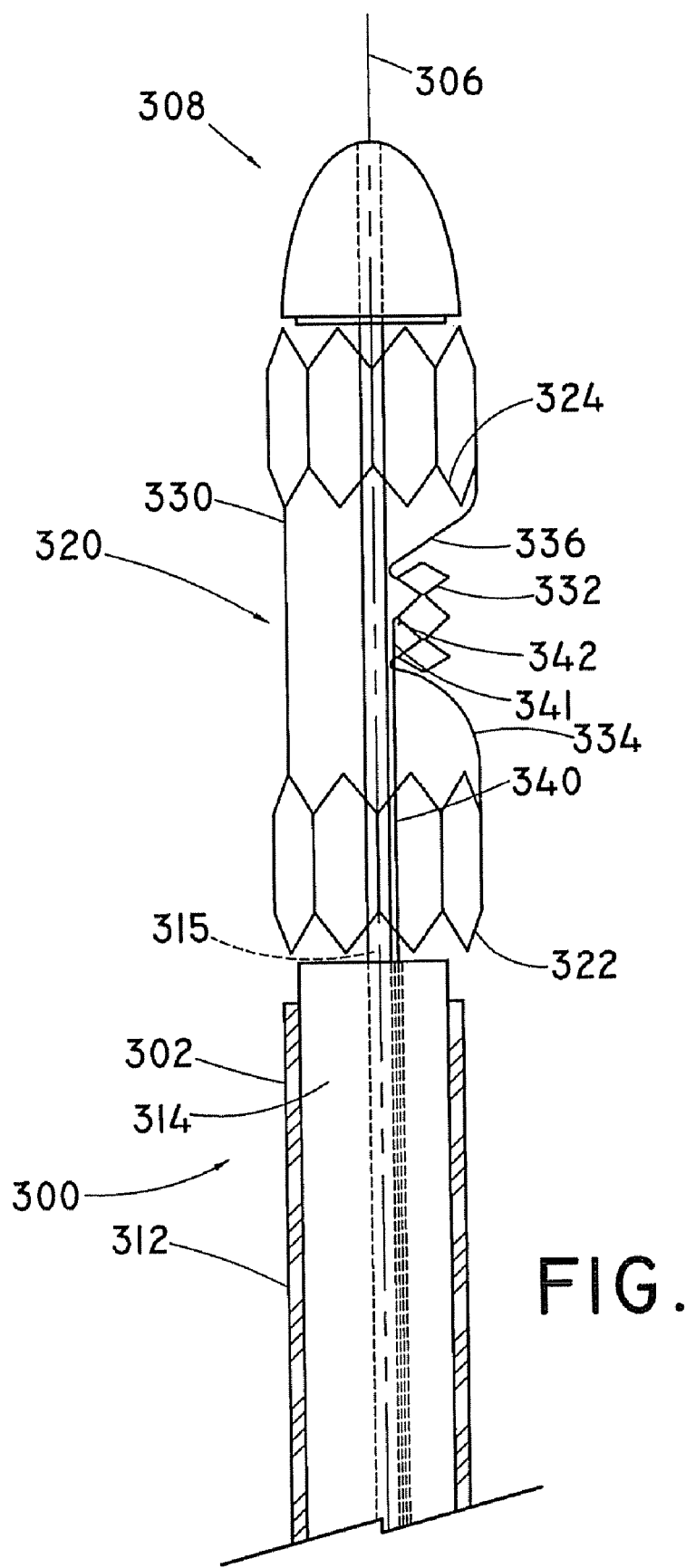
Figure 7C:
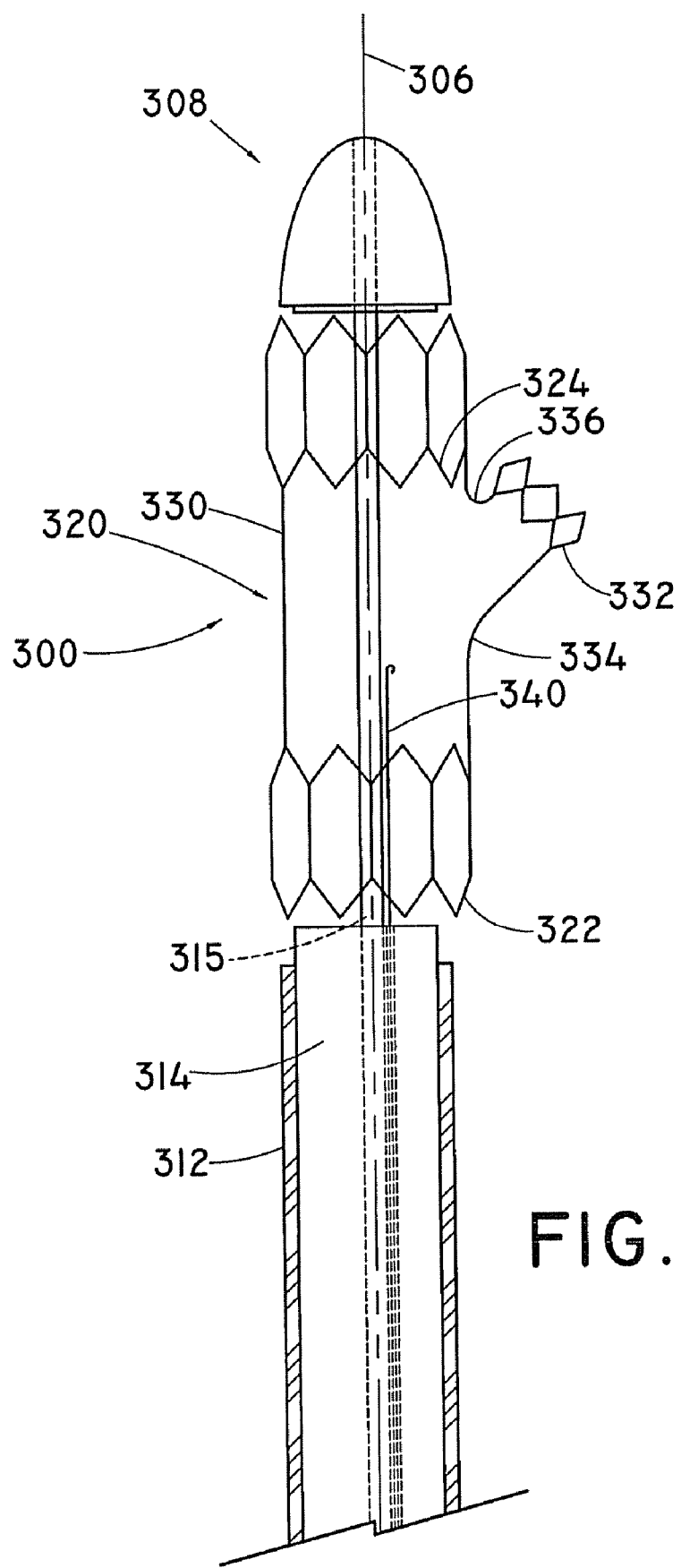

The branched vessel prosthesis can be deployed in stages within a body vessel, permitting adjustment of the relative longitudinal spacing of the primary hoop members relative to one another during the deployment process. FIGS. 7A-7C show the deployment of the branched vessel prosthesis from the delivery system 300 shown in FIGS. 5A-5C. To deploy a branched vessel prosthesis 320 in a radially compressed configuration shown in FIG. 5A, the outer sheath 312 is translated in a proximal direction relative to the inner shaft 314 and the branched vessel prosthesis 320, away from the tip portion 308. In FIG. 7A, the outer sheath 312 is translated in a proximal direction past a radially self-expanding first primary hoop member 324, permitting the radial expansion of the first primary hoop member 324 as shown. The second primary hoop member 322 remains in the radially compressed configuration. The branch hoop member 332 remains in the first position, restrained by the proximal portion 342 of the mechanical tether 340. The flexible longitudinal connecting struts 334, 336 can extend from the primary hoop members 322, 324 to the branch hoop member 332. The two primary hoop members 322, 324 can be joined by one or more primary longitudinal connecting struts 330.

To continue deployment of the branched vessel prosthesis 320, the outer sheath 312 is translated in the proximal direction relative to the inner shaft 314 and the branched vessel prosthesis 320. FIG. 7B shows the subsequent outer sheath 312 retracted proximally away from the branched vessel prosthesis 320, permitting radial self expansion of both the primary hoop members 322, 324 to define a primary lumen therebetween. The branch hoop member 332 remains in the first position between the primary hoop members 322, 324, restrained by the proximal portion 342 of the mechanical tether 340, or other retaining means discussed above. The inner diameter of the radially expanded primary hoop members 322, 324 is preferably larger than the maximum diameter of the tip 308, the outer sheath 312 around the inner shaft 314. The branch hoop member 332 in the first position remains to one side of the longitudinal axis 306 of the delivery catheter.

The branch hoop member 332 may be extended in a direction away from the longitudinal axis 306 as shown in FIG. 7C by manipulating the mechanical tether 340 so as to release the branch hoop member 332 from the first position (FIG. 7B) to the second position in FIG. 7C. The flexible longitudinal connecting struts 334, 336 are preferably configured to self expand in a manner to translate the branch hoop member 332 toward the second position upon release of the mechanical tether 340. Preferably, the branch hoop member 332 is released into a branched vessel at a point of treatment. After deployment of the branched vessel prosthesis 332, the outer sheath 312 may be translated along the longitudinal axis relative to the inner shaft 314 toward the tip 308. The delivery catheter may subsequently be removed from the body vessel, leaving the branched vessel prosthesis at a branched vessel.

The method may also include one or more of the following steps: determining the size of the first body vessel and the second body vessel; assembling the support frame in the expanded configuration by selecting the primary hoop members sized to fit within the first body vessel at the point of treatment, and attaching the at least one primary longitudinal strut to connect the primary hoop members, and selecting the branch hoop member sized to fit within the second body vessel at the point of treatment, and attaching the at least one flexible strut to the branch hoop member to connect the branch hoop member to at least one primary hoop member to form the branched vessel prosthesis in the branch expanded configuration with the branch hoop member in the second position; translating the branch hoop member from the second position to the first position by bending the at least one flexible strut; radially compressing the branched vessel prosthesis into the compressed configuration while maintaining the branch hoop member in the first position prior to inserting the branched vessel prosthesis into the body.

The branched vessel prosthesis as described herein may be delivered to any suitable body vessel, such as a vein, artery, biliary duct, ureteral vessel, body passage or portion of the alimentary canal. While many preferred embodiments discussed herein discuss implantation of a branched vessel prosthesis in a vein, other embodiments provide for implantation within other body vessels. In another matter of terminology there are many types of body canals, blood vessels, ducts, tubes and other body passages, and the term "vessel" is meant to include all such passages. In some embodiments, branched vessel prosthesis having a compressed delivery configuration with a very low profile, small collapsed diameter and great flexibility, may be able to navigate small or tortuous paths through a variety of body vessels. A low-profile branched vessel prosthesis may also be useful in coronary arteries, carotid arteries, vascular aneurysms, and peripheral arteries and veins (e.g., renal, iliac, femoral, popliteal, sublavian, aorta, intercranial, etc.). Other nonvascular applications include gastrointestinal, duodenum, biliary ducts, esophagus, urethra, reproductive tracts, trachea, and respiratory (e.g., bronchial) ducts.

The configuration of the branched vessel prosthesis may be selected for a particular method of treatment. For example, in the peripheral vasculature, vessels are generally more compliant and typically experience dramatic changes in their cross-sectional shape during routine activity. Medical devices for implantation in the peripheral vasculature should retain a degree of flexibility to accommodate these changes of the vasculature. Accordingly, medical devices according to the invention intended for implantation in the peripheral vasculature, such as prosthetic venous valves, advantageously include a self-expandable support frame.

The prosthetic branched vessel devices of the first embodiment are desirably adapted for deployment within the vascular system, and in certain preferred embodiments, are adapted for deployment within the venous system. Accordingly, a prosthetic branched vessel device may be configured as a venous valve, for example, for placement within veins of the legs or feet, to treat venous insufficiency. The medical devices can be placed in any medically appropriate location for a given application. For example, in some embodiments, the medical device can serve as part of a venous valve prosthetic and be implanted in the femoral vein, including at the proximal (groin), mid (mid section) or distal (adjacent to the knee) portions of the vein.

The methods and devices described herein are useful in treating a variety of medical conditions, including methods of treating conditions related to undesirable levels of retrograde fluid flow across a valve within a body cavity, especially near a branched site, such as venous valve related condition. Other areas of treatment are in bifurcated veins that split or form to bypass thrombosed regions of a primary vessel and reconnect at another point and the junction of the deep vein or superficial veins and secondary and/or collateral veins.

Those of skill in the art will appreciate that other embodiments and variants of the structures and methods described above can be practiced within the scope of the present invention. It is therefore intended that the foregoing detailed description be regarded as illustrative rather than limiting, and that it be understood that it is the following claims, including all equivalents, that are intended to define the spirit and scope of this invention.

The invention claimed is:

1. A branched vessel prosthesis comprising:
   two primary hoop members spaced apart by a longitudinal distance and at least one primary longitudinal strut coupling the two primary hoop members to define a primary lumen through the primary hoop members about a longitudinal axis, each of the primary hoop members being movable between a radially compressed configuration having a first diameter and a radially expanded configuration having a second diameter such that the primary lumen has a radially compressed inner diameter and a radially expanded inner diameter, and
   a branch hoop member and at least one flexible member coupling the branch hoop member with at least one of the primary hoop members, the branch hoop member having an axial length that is less than the radially compressed inner diameter of the primary lumen, and a diameter that is less than the longitudinal distance between the primary hoop members, the branch hoop member being movable between a first position and a second position, where in the first position the at least one flexible member being bowed inward such that, the entire branch hoop member is disposed within the primary lumen and between the primary hoop members when each of the primary hoop members is in the radially compressed configuration, where in the second position the branch hoop member is disposed outside the primary lumen when the primary hoop members are in the radially expanded configuration, the branch hoop member in the second position defining a branch lumen about a branch axis in communication with the primary lumen.

2. The prosthesis of claim 1, wherein an angle is formed between the longitudinal axis and the branch axis, and the at least one flexible member has a bend configured to conform around said angle.

3. The prosthesis of claim 1, further comprising a graft material, the graft material having a primary portion attached to the primary hoop members and a secondary portion attached to the branch hoop member.

4. The prosthesis of claim 1, further comprising a valve leaflet extending from a base to a free edge, the valve leaflet base being attached to one of the primary hoop members, the free edge being movable within the primary lumen between an open position permitting fluid flow in an antegrade direction through the primary lumen and a closed position inhibiting fluid flow in a retrograde direction opposite the antegrade direction through the primary lumen.

5. The prosthesis of claim 4, where the primary hoop members include a first primary hoop member proximal to a second primary hoop member, the valve leaflet being attached to the first primary hoop member.

6. The prosthesis of claim 4, further comprising a second valve leaflet extending from a base to a free edge, the second valve leaflet base being attached to the branch hoop member, the second valve leaflet free edge movable within the branch lumen between an open position permitting fluid flow in a first direction through the branch lumen and a closed position inhibiting fluid flow in a second direction opposite the first direction through the branch lumen.

7. The prosthesis of claim 1, further comprising a valve leaflet extending from a base to a free edge, the valve leaflet base being attached to branch hoop member, the free edge movable within the branch lumen between an open position permitting fluid flow in a first direction through the branch lumen and a closed position reducing or preventing fluid flow in a second direction opposite the first direction through the branch lumen.

8. The prosthesis of claim 1, wherein the length of the branch hoop member is about 25% to 75% of the first diameter of the primary hoop members in the radially compressed configuration.

9. A branched vessel prosthesis delivery system comprising:
   a delivery catheter extending from a proximal end to a distal end about a longitudinal axis, the delivery catheter including an outer sheath enclosing an inner shaft portion, the outer sheath being translatable along the longitudinal axis relative to the inner shaft; and
   a branched vessel prosthesis having a support frame comprising two primary hoop members spaced apart by a longitudinal distance and at least one primary longitudinal strut coupling the two primary hoop members to define a primary lumen through the primary hoop members, each of the primary hoop members being movable between a radially compressed configuration having a first diameter and a radially expanded configuration having a second diameter such that the primary lumen has a radially compressed inner diameter and a radially expanded inner diameter, and a branch hoop member and at least one flexible member coupling the branch hoop member with at least one of the primary hoop members, the branch hoop member having an axial length that is less than the radially compressed inner diameter of the primary lumen, and a diameter that is less than the longitudinal distance between the primary hoop members, the branch hoop member being movable between a first position and a second position, where in the first position the at least one flexible member being bowed inward such that, the entire branch hoop member is disposed within the primary lumen and between the primary hoop members when each of the primary hoop members is in the radially compressed configuration, where in the second position the branch hoop member is outside the primary lumen when the primary hoop members are in the radially expanded configuration, the branch hoop member in the second position defining a branch lumen in communication with the primary lumen,
   wherein the outer sheath and the inner shaft portion are configured and oriented such that a retaining region is formed to receive the branched vessel prosthesis with the primary hoop members in the radially compressed configuration and the branch hoop member in the first position.

10. The delivery system of claim 9, where each of the primary hoop members in the radially compressed configuration is disposed around the inner shaft portion, and the branch hoop member in the first position is disposed between the outer sheath and the inner shaft portion.

11. The delivery system of claim 9, further comprising a tethering device having a wire member extending along the delivery catheter and a grasping member coupled to the wire member and removably attached to the branch hoop member, the tethering device being configured to controllably retain the branch hoop member in the first position independent of the movement of the primary hoop members between the radially compressed configuration and the radially expanded configuration.

12. The delivery system of claim 9, further comprising a trigger wire extending along the delivery catheter and removably attached to the branch hoop member, the trigger wire configured to controllably retain the branch hoop member in the first position independent of the movement of the primary hoop members between the radially compressed configuration and the radially expanded configuration.

13. The delivery system of claim 12, wherein the trigger wire includes a loop removably attached to a distal portion of the branch hoop member, the loop configured to center the distal portion of the branch hoop member into contiguous contact and to urge the distal portion adjacent the inner shaft when the branch hoop member is in the first position.

14. The delivery system of claim 12, wherein the trigger wire is removably attached to a proximal portion of the branch hoop member such that the proximal portion of the branch hoop member is adjacent the inner shaft when the branch hoop member is in the first position.

15. The delivery system of claim 9, where the branched vessel prosthesis further comprises a valve leaflet to regulate fluid flow within the primary lumen, the valve leaflet having a base attached to one of the primary hoop members and a free edge extending into the primary lumen.

16. The delivery system of claim 15, where the branched vessel prosthesis further comprises a second valve leaflet to regulate fluid flow within the branch lumen, the valve leaflet having a base attached to the branch hoop member and a free edge extending into the branch lumen.

* * * * *